US012741058B2

(12) United States Patent
Bitar

(10) Patent No.: US 12,741,058 B2
(45) **Date of Patent: *Sep. 22, 2026**

(54) METHODS OF BIOENGINEERING INTERNAL ANAL SPHINCTER CONSTRUCTS

(71) Applicant: Wake Forest University Health Sciences, Winston-Salem, NC (US)

(72) Inventor: Khalil Bitar, Winston-Salem, NC (US)

(73) Assignee: Wake Forest University Health Sciences, Winston-Salem, NC (US)

(*) Notice: Subject to any disclaimer, the term of this patent is extended or adjusted under 35 U.S.C. 154(b) by 1079 days.

This patent is subject to a terminal disclaimer.

(21) Appl. No.: 17/294,312

(22) PCT Filed: Nov. 14, 2019

(86) PCT No.: PCT/US2019/061551

§ 371 (c)(1),
(2) Date: May 14, 2021

(87) PCT Pub. No.: WO2020/102590

PCT Pub. Date: May 22, 2020

(65) Prior Publication Data

US 2022/0016316 A1 Jan. 20, 2022

Related U.S. Application Data

(60) Provisional application No. 62/768,519, filed on Nov. 16, 2018.

(51) Int. Cl.

| | |
|---|---|
| ***A61L 27/36*** | (2006.01) |
| ***A61B 10/04*** | (2006.01) |
| ***C12N 5/071*** | (2010.01) |

(52) U.S. Cl.

CPC ......... *A61L 27/367* (2013.01); *A61L 27/3629* (2013.01); *A61L 27/3687* (2013.01); *A61L 27/3691* (2013.01); *C12N 5/0697* (2013.01); *A61B 10/04* (2013.01); *C12N 2502/088* (2013.01); *C12N 2502/1347* (2013.01); *C12N 2533/54* (2013.01)

(58) Field of Classification Search

CPC . A61L 27/367; A61L 27/3629; A61L 27/3687

See application file for complete search history.

(56) References Cited

U.S. PATENT DOCUMENTS

| | | | | |
|---|---|---|---|---|
| 4,505,266 | A | 3/1985 | Yannas et al. | |
| 5,190,878 | A | 3/1993 | Wilhelm | |
| 5,231,169 | A | 7/1993 | Constantz et al. | |
| 5,605,835 | A | 2/1997 | Hu et al. | |
| 5,688,687 | A | 11/1997 | Palsson et al. | |
| 5,888,807 | A | 3/1999 | Palsson et al. | |
| 5,985,653 | A | 11/1999 | Armstrong et al. | |
| 6,001,642 | A | 12/1999 | Tsao | |
| 6,419,920 | B1 | 7/2002 | Mineau-Hanschke | |
| 7,029,689 | B2 | 4/2006 | Berglund et al. | |
| 7,368,279 | B2 | 5/2008 | Bitar et al. | |
| 8,197,553 | B2 * | 6/2012 | Gazit | A61L 27/507 623/23.75 |
| 9,675,646 | B2 * | 6/2017 | Bitar | A61L 27/50 |
| 9,862,924 | B2 | 1/2018 | Bitar | |
| 9,896,656 | B2 | 2/2018 | Bitar | |
| 9,993,505 | B2 | 6/2018 | Bitar | |
| 10,377,985 | B2 | 8/2019 | Bitar | |
| 10,828,143 | B2 | 11/2020 | Bitar | |
| 2003/0031651 | A1 | 2/2003 | Lee et al. | |
| 2003/0072741 | A1 | 4/2003 | Berglund et al. | |
| 2003/0113812 | A1 | 6/2003 | Hemperly | |
| 2004/0197375 | A1 | 10/2004 | Rezania et al. | |
| 2005/0209687 | A1 | 9/2005 | Sitzmann et al. | |
| 2006/0134076 | A1 | 6/2006 | Bitar et al. | |
| 2006/0153815 | A1 | 7/2006 | Seyda et al. | |

(Continued)

FOREIGN PATENT DOCUMENTS

| | | | |
|---|---|---|---|
| GB | 2523399 | A | 8/2015 |
| JP | 2004528101 | A | 9/2004 |

(Continued)

OTHER PUBLICATIONS

Phillips, M. et al. Small intestine tissue sample. MedlinePlus (database online], Apr. 11, 2018. 4 [retrieved on Jan. 6, 2020). Retrieved from https:/medlineplus.gov/ency/imagepages/9927.html.; referenced in IDS submitted Jun. 28, 2021, (Year: 2018).*

Bohl JL, Zakhem E, Bitar KN. Successful Treatment of Passive Fecal Incontinence in an Animal Model Using Engineered Biosphincters: A 3-Month Follow-Up Study. Stem Cells Transl Med. Sep. 2017;6(9):1795-1802. doi: 10.1002/sctm.16-0458. Epub Jul. 5, 2017. PMID: 28678378; PMCID: PMC5689776. (Year: 2017).*

Phillips, M. et al. Small intestine tissue sample. MedlinePlus (database online], Apr. 11, 2018. 4 [retrieved on Jan. 6, 2020). Retrieved from https:l/medlineplus.gov/ency/imagepages/9927.html .; referenced in IDS submitted Jun. 28, 2021, (Year: 2018 (Year: 2018).*

Raghavan et al. (Gastroenterology. Jul. 2011;141(1):310-9. doi: 10.1053/j.gastro.2011.03.056. Epub Apr. 2, 2011.) (Year: 2011).*

Rego et al. (Tissue Eng Part A. Dec. 30, 2015;22(1-2):151-160. doi: 10.1089/ten.tea.2015.0194) (Year: 2015).*

(Continued)

*Primary Examiner* — Christopher M Babic
*Assistant Examiner* — Joel D Levin
(74) *Attorney, Agent, or Firm* — Joseph F. Murphy; Reza Mollaaghababa; Potomac Law Group, PLLC

(57) ABSTRACT

The present disclosure provides methods of bioengineering sphincters having autologous smooth muscle cells isolated from human internal anal sphincter and autologous enteric neurospheres (neural progenitor cells) isolated from human small intestine (jejunum). The isolated neural progenitor cells and smooth muscle cells are co-cultured using dual layered hydrogels and allowed to form circular, intrinsically innervated internal anal sphincter constructs. Such innervated internal anal sphincter constructs, bioengineered internal anal sphincter constructs are useful as additive implants in the treatment of fecal incontinence.

18 Claims, 31 Drawing Sheets

(56) References Cited

U.S. PATENT DOCUMENTS

| | | | |
|---|---|---|---|
| 2007/0025972 | A1 | 2/2007 | Rodriguez |
| 2007/0128171 | A1 | 6/2007 | Tranquillo et al. |
| 2007/0269481 | A1 | 11/2007 | Li et al. |
| 2007/0275362 | A1 | 11/2007 | Edinger |
| 2008/0031850 | A1 | 2/2008 | Bader |
| 2008/0102438 | A1 | 5/2008 | Yannas et al. |
| 2009/0317416 | A1 | 12/2009 | Mamula |
| 2010/0010290 | A1 | 1/2010 | Stephens et al. |
| 2010/0131075 | A1 | 5/2010 | Ludlow et al. |
| 2010/0184183 | A1 | 7/2010 | Schussler |
| 2011/0151011 | A1 | 6/2011 | Flynn |
| 2014/0271905 | A1 | 9/2014 | Bitar |
| 2014/0377232 | A1 | 12/2014 | Bitar |
| 2014/0379083 | A1 | 12/2014 | Bitar |
| 2016/0017285 | A1 | 1/2016 | Bitar |
| 2016/0134076 | A1 | 5/2016 | Arai et al. |
| 2017/0319325 | A1 | 11/2017 | La Francesca et al. |
| 2018/0093016 | A1 | 4/2018 | Bitar |
| 2018/0155684 | A1 | 6/2018 | Bitar |
| 2018/0256647 | A1 | 9/2018 | Bitar |
| 2019/0015190 | A1 | 1/2019 | Bitar |
| 2020/0024572 | A1 | 1/2020 | Bitar |
| 2021/0137668 | A1 | 5/2021 | Bitar |

FOREIGN PATENT DOCUMENTS

| | | | | |
|---|---|---|---|---|
| WO | 0149827 | A1 | 7/2001 | |
| WO | 02087411 | A2 | 11/2002 | |
| WO | 03029418 | A2 | 4/2003 | |
| WO | 2010040129 | A2 | 4/2010 | |
| WO | 2010072417 | A2 | 7/2010 | |
| WO | 2011059920 | A2 | 5/2011 | |
| WO | 2011102991 | A1 | 8/2011 | |
| WO | 2011119804 | A2 | 9/2011 | |
| WO | 2012064369 | A1 | 5/2012 | |
| WO | 2013116446 | A1 | 8/2013 | |
| WO | 2013116479 | A1 | 8/2013 | |
| WO | 2014145653 | A2 | 9/2014 | |
| WO | WO-2017117229 | A1 * | 7/2017 | ........... C12N 5/0697 |
| WO | 2018052953 | A1 | 3/2018 | |
| WO | 2020102590 | A1 | 5/2020 | |

OTHER PUBLICATIONS

Phillips, M. et al. Small intestine tissue sample. MedlinePlus (database online], Apr. 11, 2018. 4 [retrieved on Jan. 6, 2020). Retrieved from https:l/medlineplus.gov/ency/imagepages/9927. html.; referenced in IDS submitted Jun. 28, 2021, (Year: 2018).*

Bagyanszki et al.,"Diabetes-Related Alterations in the Enteric Nervous System and its Microevirment", World Journal of Diabetes, vol. 3, May 15, 2012, pp. 80-93.

Bitar et al., Receptors on smooth muscle cells: characterization by contraction and specific antagonists, Am. J. Physiol., 242:G400-G407 (1982).

Bitar, Aging and Neural Control of the GI Tract V. Aging and gastrointestinal smooth muscle: from signal transduction to contractile proteins, Am. J. Physiol., 284:GI-G7 (2003).

Bitar, HSP27 phosphorylation and interaction with actinmyosin in smooth muscle contraction, Am. J. Physiol., 282: G894-G903 (2002).

Buijtenhuijs et al., "Tissue engineering of blood vessels : characterization of smooth-muscle cells for culturing on collagen- and-elast in based scaffods", Biotechnol. Appl Apr. 2004 vol. 39, pp. 141-149. See Abstract: materials and methods 144, 146.

Carson, Histotechnology: A Self-Instructional Text, Chicago: American Society for Clinical Pathology Press ( 1997), table of contents, 8 pages.

Dahm et al.,Substance P Responsiveness of Smooth Muscle Cells is Regulated by the Integrin Ligand Thrombospondin, Proc. Natl. Acad. Sci. USA vol. 93 Feb. 6, 1996, pp. 1276-1281.

Davis et al., Basic Methods in Molecular Biology, Elsevier (1986),table of contents, 5 pages.

Edelman, Vascular Tissue Engineering Designer Arteries, Circ. Res., 85:1115-1117 (1999).

European Extended Supplementary Search Report received in EP Application No. 14763675.7 dated Aug. 12, 2016; 9 pages.

European Office Action received in EP Application No. 13743292.8 dated Jul. 18, 2017; 6 pages.

European Search Report received in EP Application No. 13743292.8 dated Aug. 18, 2015; 7 pages.

Evers et al., Is there a nitrergic modulation of the rat external anal Sphincter? Exp Physiol vol. 98.2 (2013) pp. 397-404.

Fujimiya et al., "Peptidergic Regulation of Gastrointestinal Motility in Rodents," Peptides, vol. 21, Oct. 2000, pp. 1565-1582.

Geisbauer et al., "Transplantation of Enteric Cells into the Rodent Stomach with Basic Fibroblast Growth Factor", Cell Sci Ther; Therapy, vol. .2. Issue 1, Mar. 10, 2011, pp. 1-6.

Gilmont, RR. et al. Bioengineering of Physiologically Functional Intrinsically Innervated Human Internal Anal Sphincter Constructs. Tissue Eng. Part A. Jun. 1, 2014, vol. 20, No. 11-12, pp. 1603-1611.

Goeddel, Gene Expression Technology: Methods in Enzymology 185, Academic Press, San Diego, CA (1990), table of contents, 11 pages.

Gorenne et al., Inhibition of p42 and p44 MAP kinase does not alter smooth muscle contraction in swine carotid artery, Am. J. Physiol., 5:H131-H138 (1998).

Hansen et al.,"Characterization of Collagen Thin Films for Von Willebrand Factor Binding and Platelet Ahesion," Langmuir, vol. 27, Oct. 3, 2011, pp. 13648-13658.

International Preliminary Report on Patentability and Written Opinion received in PCT/US2013/024024 dated Aug. 5, 2014; 8 pages.

International Preliminary Report on Patentability and Written Opinion, PCT/US2013/024080, dated Aug. 5, 2014 (9 pages).

International Preliminary Report on Patentability, PCT/US2019/061551, dated May 27, 2021, 9 Pages.

International Search Report and Written Opinion received in PCT/US2014/030456 dated Aug. 29, 2014; 10 pages.

International Search Report and Written Opinion received in PCT/US2016/068891 dated Mar. 29, 2017; 9 pages.

International Search Report and Written Opinion, PCT/US2013/024024, dated May 15, 2013 (11 pages).

International Search Report and Written Opinion, PCT/US2013/024080, dated Jun. 2, 2013 (11 pages).

International Search Report and Written Opinion, PCT/US2019/061551, dated Jan. 24, 2020, 10 pages.

Japanese Office Action received in JP Application No. 2014-555699 dated Jul. 25, 2017; 5 pages.

Keef et al., Functional role of vasoactive intestinal polypeptide in inhibitory motor innervation in the mouse internal anal sphincter. J Physiol Mar. 15, 2013; 591(6): 1489-506.

L'Heureux et al., "A completely Biological Tissue-Engineered Human Blood Vessel", The FASEB Journal, vol. 12 Jan. 1998 pp. 47-56.

Madihally, Sundararajian et al. "Porous Chitosan Scaffolds for Tissue Engineering", Biomaterials 20 pp. 1133-1142 (1999).

Office Action received in U.S. Appl. No. 14/216,391 dated Feb. 3, 2017; 6 pages.

Office Action received in U.S. Appl. No. 14/777,335 dated Apr. 13, 2016; 18 pages.

Office Action received in U.S. Appl. No. 14/777,335 dated Oct. 31, 2016; 15 pages.

Office Action received in U.S. Appl. No. 16/066,492 dated Apr. 1, 2020, 11 pages.

Orlando et al., Regenerative medicine as applied to solid organ transplantation current status and future challenges. Transplant International vol. 24 No. 3 Mar. 2011 pp. 223-232.

Phillips, M. et al. Small intestine tissue sample. MedlinePlus [database online], Apr. 11, 2018. [retrieved on Jan. 6, 2020], Retrived from https://medlineplus.gov/ency/imagepages/9927.htm., pp. 2.

Raghavan et al., "Bioengineered Three-Dimensional Physiological Model of Colonic Longitudinal Smooth Muscle In vitro," Tissue Engineering: Part C vol. 16 No. 5, Oct. 2010, pp. 999-1009.

(56) References Cited

OTHER PUBLICATIONS

Raghavan et al., Successful implantation of bioengineered, intrinsically innervated human internal anal sphincter Gastroenterology, 141, Jul. 2011 pp. 310-319.
Raghavan et al., "The Influence of Extracellular Matrix Composition on the Differentiation of Neuronal Subtypes inTissue Engineered Innervated Intestinal Smooth Muscle Sheets," Biomaterials, vol. 35, Jun. 11, 2014 pp. 7429-7440.
Raghavan et al., Neuroglial differentiation of adult enteric neuronal progenitor cells as function of extracellular matrix compositon Biomaterials, vol. 34 No. 28 Sep. 2013 pp. 6649-6658.
Somara et al., Bioengineered Internal Anal Sphincter Derived From Isolated Human Internal Anal Sphineter Muscle Cells. Gastroenterology 2009, pp. 53-61.
Tulla et al., "Selective Binding of Collagen Subtypes by Integrin Alpha 1-1, Alpha 2-1, and Alpha 10-1 Domains," The Journal of Biological Chemistry, vol. 276 No. 51 Sep. 25, 2001 pp. 48206-48212.
Ward et al., "Interstitial Cells of Cajal Mediate Cholinergic Neurotransmission From Enteric Motor Neurons," The Journal of Nueroscience vol. 20 Feb. 15, 2000 pp. 1393-1403.
Zakhem et al., "Transplantation of a human Tissue-Engineered Bowel in an Athymic Rat Model", Tissue Engineering Jun. 2017, vol. 00, pp. 1-9.
Zakhem, E et al. Successful Implantation of an Engineered Tubular Neuro-Muscular Tissue Composed of Human Cells and Chitosan Scaffold. Jun. 19, 2015; Surgery 158(6); 1598-1608.
Zhang, et al. "A Sandwich Tubular Scaffold Derived From Chitosan for Blood Vessel Tissue Engineering" Wiley Periodicals, Inc. pp. 277-284 (2006).
Deleyrolle, L. et al., "Isolation, Expansion, and Differentiation of Adult Mammalian Neural Stem and Progenitor Cells Using the Neurosphere Assay," Neural Cell Transplantation, 91-101 (2009).
Hecker, L. et al., "Development of a three-dimensional physiological model of the internal anal sphincter bioengineered in vitro from isolated smooth muscle cells," Am J Physiol Gastrointest Liver Physiol., vol. 289: G188-G196 (2005).
U.S. Appl. No. 14/216,391, filed Mar. 17, 2014, Khalil Bitar.
U.S. Appl. No. 15/875,717, filed Jan. 19, 2018, Khalil Bitar.
U.S. Appl. No. 16/538,076, filed Aug. 12, 2019, Khalil Bitar.
U.S. Appl. No. 14/777,335, filed Sep. 15, 2015, Khalil Bitar.
U.S. Appl. No. 16/066,492, filed Jun. 27, 2018, Khalil Bitar.
U.S. Appl. No. 17/066,233, filed Oct. 8, 2020, Khalil Bitar.
U.S. Appl. No. 15/808,338, filed Nov. 9, 2017, Khalil Bitar.
U.S. Appl. No. 14/375,818, filed Jul. 31, 2014, Khalil Bitar.
U.S. Appl. No. 14/375,812, filed Jul. 31, 2014, Khalil Bitar.
U.S. Appl. No. 15/976,569, filed May 10, 2018, Khalil Bitar.
Astill T Pet al: "Promisuous binding of proinsulin peptides t type 1 diabetes-permissive and- protective HLA class II molecules", Diabetologia, Springer Berlin Heidelberg, Berlin/Heidelberg, vol. 46, No. 4, Apr. 1, 2003 (Apr. 1, 2003), pp. 496-503, XP008094668.
Bohl JL, Zakhem E, Bitar KN. Successful Treatment of Passive Fecal Incontinence in an Animal Model Using Engineered Biosphicters: A 3-Month Follow-Up Study. Stem Cells Tranl Med 2017 2017.
International Search Report & Written Opinion issued in International Patent Application No. PCT/IB2022/055607 issued Oct. 10, 2022.
M. Schlosser et al: "Pro- and anti-inflammatory cytokine production by autoimmune T cells against preproinsulin in HLA-DRB1*04, DQ8 Type 1 diabetes", Diabetologia, vol. 47, No. 3, Mar. 1, 2004 (Mar. 1, 2004), pp. 439-450, XP055187192.
Sarmay Gabriella et al: "Biologia Futura: Emerging antigen-specific therapies for autoimmune diseases", Biologia Futura, vol. 72, No. 1, Mar. 1, 2021 (Mar. 1, 2021), pp. 15-24, XP55966428.
Tian Jide et al: "Designing Personalized Antigen-Specific Immunotherapies for Autoimmune Diseases—The Case for Using Ignored Target Cell Antigen Determinants", Cells, vol. 11, No. 7, Mar. 23, 2022 (Mar. 23, 2022) , p. 1081, XP55966318.

* cited by examiner (A) α-smooth muscle actin (B) Smoothelin

METHODS OF BIOENGINEERING INTERNAL ANAL SPHINCTER CONSTRUCTS

CROSS REFERENCE APPLICATION

This application is a 35 U.S.C. 371 national stage filing of International Application No. PCT/US2019/061551 filed on Nov. 14, 2019, which claims priority to, and the benefit of, U.S. Provisional Application No. 62/768,519, filed Nov. 16, 2018. The entire contents of the aforementioned applications are incorporated herein by reference.

GOVERNMENT SUPPORT

This invention was made with government support under R42DK105593 awarded by National Institute of Health, National Institute of Digestive and Kidney disease (NIH/NIDDK). The government has certain rights in the invention.

BACKGROUND

The anorectum generally includes the distal portion of the digestive tract, incorporating the anal canal and the distal rectum. Anorectal continence is maintained by interplay between the enteric nervous system, smooth muscle internal anal sphincter, the striated external anal sphincter and puborectalis muscles. The internal anal sphincter contributes >70% of the basal tension required to maintain continence. An injury or any damage to the integrity of the anorectum can result in fecal incontinence, for example, an injury to the perineum may result in complete or partial destruction of the anal sphincter and distal rectum, potentially resulting in persistent incontinence or need for permanent colostomy.

SUMMARY

The present disclosure encompasses a recognition that there is a need for treating loss of function and/or damage to the internal anal sphincter resulting from injury, age, or otherwise that may cause fecal incontinence.

Among other things, in some embodiments, the present disclosure provides methods of generating an internal anal sphincter construct. In some embodiments, methods can include biopsying tissue from a subject's anorectum tissue and intestinal tissue. In some embodiments, methods can further include isolating smooth muscle cells and neural progenitor cells respectively from the biopsied anorectum and intestinal tissues. In some embodiments, methods can further includes a step of preparing a smooth muscle cell gel and a neural progenitor cell gel. In some embodiments, methods can further include seeding the gels to form a matrix on a culture plate and/or mold. In some embodiments, methods can further include contacting the gels with a differentiating media thereby forming the internal anal sphincter construct.

In some embodiments, methods of generating an internal anal sphincter construct can include a step of obtaining an anorectum tissue cell biopsy from a subject. In some embodiments, methods can include obtaining a biopsy from the subject's internal anal sphincter tissue. In some embodiments, the step of obtaining the anorectum tissue cell biopsy and/or the internal anal sphincter tissue biopsy can be performed laparoscopically.

In some embodiments, methods of generating an internal anal sphincter construct can include steps of obtaining an intestinal tissue cell biopsy from a subject. In some embodiments, methods can include obtaining a biopsy from the subject's jejunal small intestine tissue. In some embodiments, the step of obtaining the intestinal tissue cell biopsy and/or the jejunal small intestine tissue biopsy can be performed laparoscopically.

In some embodiments, methods can include a step of isolating smooth muscle cells from the anorectum tissue cell biopsy. In some embodiments, methods can include a step of isolating neural progenitor cells from the intestinal tissue cell biopsy.

In some embodiments, methods can include steps of isolating smooth muscle cells from the anorectum tissue cell biopsy. In some embodiments, steps of isolating can include a step of mechanically disaggregating the anorectum tissue cell biopsy. In some embodiments, steps of isolating can include a step of enzymatically digesting the mechanically disaggregated cell biopsy. In some embodiments, steps of isolating can include a step of washing the enzymatically digested cell biopsy. In some embodiments, the step of enzymatically digesting can include a digesting media. In some embodiments, the digesting media can include a collagenase, e.g., Collagenase type II. In some embodiments, the digesting media can include Collagenase DE, Collagenase HA, Collagenase MA, or combinations thereof. In other embodiments, other proteases can be used as an alternative or in conjunction with a collagenase.

In some embodiments, steps of isolating can include a step of centrifuging the washed enzymatically digested cell biopsy. In some embodiments, steps of isolating can include a step of recovering a pellet of smooth muscle cells. In some embodiments, steps of isolating can include a step of re-suspending the recovered pellet of smooth muscle cells in a smooth muscle cell growth medium. In some embodiments, the smooth muscle cell growth medium, for example, can include Smooth Muscle Basal Medium (Promocell), optionally supplemented with fetal bovine serum (FBS), antibiotics (e.g., Gentamicin), growth factors (e.g., hEGF and/or hbEGF) and/or insulin; or Dulbecco's Modified Eagle Medium high glucose (Invitrogen) optionally supplemented with 10% FBS, 2.5 mM L-glutamine and/or 1× antibiotic/antimycotic.

In some embodiments, methods can include, a step of culturing the isolated smooth muscle cells until a number of smooth muscle cells reaches at least one million cells. In some embodiments, methods can further include a step of counting the smooth muscle cells. In some embodiments, steps can be repeated until cell counts reach at least 250,000; at least 500,000; at least 1 million; at least 2 million; at least 2.5 million; at least 3 million; at least 3.5 million; at least 4 million; at least 4.5 million; at least 5 million; at least 7.5 million; at least 10 million; at least 15 million; at least 20 million; at least 25 million; at least 50 million; or more.

In some embodiments, methods can include steps of isolating neural progenitor cells from the intestinal tissue cell biopsy. In some embodiments, steps of isolating can include a step of mechanically disaggregating the intestinal tissue cell biopsy. In some embodiments, steps of isolating can include a step of enzymatically digesting the mechanically disaggregated cell biopsy. In some embodiments, steps of isolating can include a step of washing the enzymatically digested cell biopsy. In some embodiments, the step of enzymatically digesting can include a digesting media. In some embodiments, the digesting media can include a collagenase, e.g., a type II Collagenase and Dispase II. In some embodiments, the digesting media can include a collagenase, e.g., a type II Collagenase and BP protease.

In some embodiments, steps of isolating can include a step of filtering the enzymatically digested cell biopsy. In some embodiments, steps of isolating can include a step of recovering neural progenitor cells based on size. In some embodiments, steps of isolating can include a step of re-suspending the recovered neural progenitor cells in a neural growth medium. In some embodiments, the neural growth medium can include a Phenol Red Free Neural Basal A Medium (ThermoFisher) or a Neurobasal media (Invitrogen) optionally supplemented with 1% N2 supplement, 20 ng/ml bFGF, 20 ng/ml EGF, 1 mM L-Glutamine, and 1× antibiotic/antimycotic.

In some embodiments, methods can include, a step of culturing the isolated smooth muscle cells until a number of smooth muscle cells reaches at least one million cells. In some embodiments, methods can further include a step of counting the neural progenitor cells. In some embodiments, steps can be repeated until cell counts reach at least 250,000; at least 500,000; at least 1 million; at least 2 million; at least 2.5 million; at least 3 million; at least 3.5 million; at least 4 million; at least 4.5 million; at least 5 million; at least 7.5 million; at least 10 million; at least 15 million; at least 20 million; at least 25 million; at least 50 million; or more.

In some embodiments, methods can include a step of preparing a smooth muscle cell gel by suspending isolated smooth muscle cells in a gel matrix. In some embodiments, the smooth muscle cell gel matrix can include collagen. In some embodiments, methods can include a step of suspending the smooth muscle cells in a collagen gel. In some embodiments, methods can include suspending the expanded culture of smooth muscle cells in a gel mixture including medical grade collagen, Smooth Muscle Basal Medium (Promocell) or Dulbecco's Modified Eagle Medium (Invitrogen) and water. In some embodiments, steps include layering the smooth muscle cell/collagen gel on the gel having the neural progenitor cells. In some embodiments, methods can include a step of gelling the smooth muscle cells. In some embodiments, the gelling, for example, can occur for around for at least 45 minutes at 37° C. and 5% $CO_2$.

In some embodiments, methods can include a step of preparing a neural progenitor cell gel by suspending isolated neural progenitor cells in a gel matrix. In some embodiments, the neural progenitor cell gel matrix can include collagen and laminin. In some embodiments, methods can include a step of suspending the expanded culture of neural progenitor cells in a collagen/laminin gel. In some embodiments, the collagen/laminin gel can include medical grade collagen, recombinant laminin, Phenol Red Free Neural Basal A medium, Neuro Basal medium (Invitrogen) or Dulbecco's Modified Eagle Medium and water. In some embodiments, method steps can include gently mixing the neural progenitor cells suspension. In some embodiments, methods can include a step of gelling the neural progenitor cells in the gel mixture. In some embodiments, methods can include a step of gently swirling the plates to ensure complete coverage of the plate and the mixture. In some embodiments, steps can include gelling in an incubator until gelation is observed. In some embodiments, steps of gelling, for example, can occur for around for at least 20 minutes at 37° C. and 7% $CO_2$.

In some embodiments, methods can include a step of providing a culture plate and/or mold. In some embodiments, methods can include a step of providing a culture plate and/or mold having a central post.

In some embodiments, methods can include steps of preparing gel layers of isolated smooth muscle cells and isolated neural progenitor cells. In some embodiments, methods can include steps of providing gel layers of isolated smooth muscle cells and isolated neural progenitor cells. In some embodiments, methods can include steps of seeding a dual layer gel matrix on the culture plate and/or mold. In some embodiments, the dual layer gel can include a smooth muscle cell gel and/or a neural progenitor cell gel. In some embodiments, steps can include seeding the dual layer gel matrix in a substantially circular shape on the culture plate and/or mold. In some embodiments, steps can include seeding the dual layer gel matrix around the central post of the culture plate and/or mold. In some embodiments, methods including a step of seeding can include adding, depositing, placing, and/or pouring, etc.

In some embodiments, methods of seeding can include providing the smooth muscle cell gel and the neural progenitor cell gel. In some embodiments, methods of seeding can include a step of layering the smooth muscle cell gel and the neural progenitor cell gel in contact with one another. In some embodiments, methods can include a step of laying the neural progenitor cells onto a prepared mold. In some embodiments, methods can include a step of laying the neural progenitor cells onto the prepared mold so that the neural progenitor cells uniformly lay on the plate or the mold. In some embodiments, the step of laying the neural progenitor cells onto the prepared mold can include laying the neural progenitor cells in a substantially circular shape on the plate. In some embodiments, the step of laying the neural progenitor cells onto the prepared mold can include laying the neural progenitor cells around a central post of the mold. In some embodiments, the step of layering can include a step of depositing a smooth muscle gel layer on the culture plate and/or mold and depositing a neural progenitor cell gel layer on top of the smooth muscle cell gel layer. Alternatively, the neural progenitor cell gel layer can be deposited first, followed by the deposition of the smooth muscle cell gel layer. Additionally, multiple layers of each cell type can be deposited in an desired order.

In some embodiments, methods can include a step of contacting the dual layer gel matrix with a differentiation media, thereby forming the construct. In some embodiments, the differentiation media can include, for example, Phenol Red Free Neural Basal A Medium (ThermoFisher) or a Neurobasal-A media (Invitrogen), optionally supplemented with a B27 supplement, 1% FBS, and 1× antibiotic/antimycotic. In some embodiments, the step of contacting the matrix with the differentiation media can include adding, depositing, placing, and/or pouring, etc. In some embodiments, methods can include a step of inducing differentiation of the neural progenitor cells. In some embodiments, following the step of contacting, the differentiation media can induce differentiation in the neural progenitor cells present in the matrix. In some embodiments, the step of contacting the matrix with differentiation media can further include a step of forming the construct having of directionally oriented smooth muscle cells.

In some embodiments, methods of generating an internal anal sphincter construct can include a step of removing the construct from the culture plate and/or mold. In some instances, the construct can be rinsed e.g., to remove growth and/or differentiation media especially to remove FBS, prior to removal of the construct from the mold. In some embodiments, methods can include a step of implanting at least one innervated anal sphincter construct into a subject. In some embodiments, methods can include a step of implanting more than one construct into a subject.

In some embodiments, bioengineered internal anal sphincter constructs formed in accordance with the present disclosure are useful for implantation in a subject. In some embodiments, at least one of these constructs is useful as an implant in the treatment of fecal incontinence. In some embodiments, a plurality of these constructs, for example, more than one, is useful as an implant in the treatment of fecal incontinence. In some embodiments, at least two of these constructs in conjunction are useful in an implant in the treatment of fecal incontinence. In some embodiments, at least three of these constructs in conjunction are useful in an implant in the treatment of fecal incontinence. In some embodiments, at least four of these constructs in conjunction are useful in an implant in the treatment of fecal incontinence. In some embodiments, at least five or more of these constructs in conjunction are useful in an implant in the treatment of fecal incontinence.

The foregoing and other advantages, aspects, embodiments, features, and objects of the present disclosure will become more apparent and better understood by referring to the following detailed description when read in connection with the accompanying drawings.

BRIEF DESCRIPTION OF THE DRAWINGS

A person of ordinary skill in the art will understand that the drawing, described below, is for illustration purposes only. The drawing are not intended to limit the scope of the Applicant's teachings in any way. It is emphasized that, according to common practice, various features of the drawing are not necessarily to scale. On the contrary, the dimensions of the various features are or may be arbitrarily expanded or reduced for clarity. Included in the drawing are the following figures:

FIG. 1A depicts smooth muscle cells grown in culture and having acquired their normal spindle like morphology. FIG. 1B depicts smooth muscle cells stained positive for α-smooth muscle actin. FIG. 1C depicts smoothelin, a smooth muscle specific marker indicating that the cells acquired their mature phenotype;

FIG. 3A is a bright-field image of neurosphere formation while FIG. 3B shows the same cells positively stained for $p75^{NTR}$. FIG. 3C is another bright-field image of neurosphere formation while FIG. 3D shows the same cells positively stained for Sox2. FIG. 3E is another bright-field image of neurosphere formation while FIG. 3F shows the same cells positively stained for Nestin;

FIG. 6A depicts stained positive for smooth muscle actin (scale bar 50 μm). FIG. 6B depicts positive βIII tubulin stain (scale bar 20 μm);

FIG. 7A depicts Smoothelin data. FIG. 7B depicts βIII tubulin data;

FIG. 9A depicts basal tone data following an addition of KCl induced smooth muscle depolarization followed by a robust contraction. FIG. 9B depicts basal tone data following neural-mediated relaxation of smooth muscle;

FIG. 10A depicts a circumferential incision was made around the anocutaneous junction of the anal canal. FIG. 10B depicts engineered autologous bioengineered internal anal sphincter constructs were placed in the intersphincteric space. FIG. 10C depicts engineered autologous bioengineered internal anal sphincter constructs were stacked circumferentially around the injury site as full muscle sphincters;

FIG. 11A shows the anal basal pressure. FIG. 11B shows the RAIR results;

FIG. 12A shows the anal basal pressure. FIG. 12B shows the RAIR results;

FIG. 13A shows the anal basal pressure. FIG. 13B shows the RAIR results;

FIG. 14A depicts exemplary data showing anal basal pressure results for the different doses over time following implantation; FIG. 14B depicts exemplary data showing RAIR results for the different doses over time following implantation;

FIG. 15A depicts H&E staining. FIG. 15B depicts Masson's trichrome staining. Scale bar 500 μm;

FIG. 16A depicts transverse sections of implanted internal anal sphincter. FIG. 16B depicts implanted smooth muscle cells. FIG. 16C depicts a proximal area of the implanted internal anal sphincter. FIG. 16D depicts a proximal area to the implant was positive to smoothelin. All the images are counterstained with DAPI nuclear stain. (scale bar 100 μm);

FIG. 17A depicts transverse sections of internal anal sphincter constructs. FIG. 17B depicts immunoreactivity with βIII tubulin. In the proximal region, FIG. 17C depicts the transduced neural progenitor cells migration. FIG. 17D depicts expressing βIII tubulin. FIG. 17E depicts migration beyond 2 mm. FIG. 17F depicts native neuron displayed βIII tubulin expressions. All the images counterstained with DAPI nuclear stain; scale bar—200 μm;

FIG. 18A depicts smooth muscle cells that proliferated and acquired a normal spindle-like morphology. FIG. 18B depicts smoothelin, a smooth muscle specific marker indicating that the cells acquired their mature phenotype;

FIG. 19A depicts flow cytometry analysis of α-smooth muscle actin. FIG. 19B depicts flow cytometry analysis of Smoothelin;

FIG. 21A depicts isolated neural progenitor cells. FIG. 21B depicts neural progenitor cells stained positive for $p75^{NTR}$, neural crest-derived marker. FIG. 21C depicts a merged image;

FIG. 23A depicts a silicone mold and/or plate that is provided. FIG. 23B depicts a neural progenitor cell gel uniformly laid onto the prepared mold around the central post. FIG. 23C depicts the smooth muscle cell gel layered on top of the gel containing the neural progenitor cells. FIG. 23D depicts smooth muscle cells having contracted both gels into a ring-like structure around the post to form one bioengineered internal anal sphincter construct;

FIG. 24A depicts exemplary data showing glucose consumption in bioengineered human internal anal sphincter constructs. FIG. 24B depicts exemplary data showing lactate production in bioengineered human internal anal sphincter constructs;

FIG. 25A depicts basal tone data following treatment with KCl. FIG. 25B depicts basal tone data following treatment with exogenous Acetylcholine. FIG. 25C depicts basal tone data following treatment with electrical field stimulation. FIG. 25D depicts basal tone data following treatment with nitric oxide synthase inhibitor, N(ω)-nitro-L-arginine methyl ester (L-NAME; 300 μM, nNOS inhibitor) followed by electrical field stimulation;

FIG. 27A depicts bioengineered human internal anal sphincter constructs stained positive for smooth muscle actin. FIG. 27B depicts a positive stain for βIII tubulin;

DETAILED DESCRIPTION

Figures 1A, 1B, 1C:
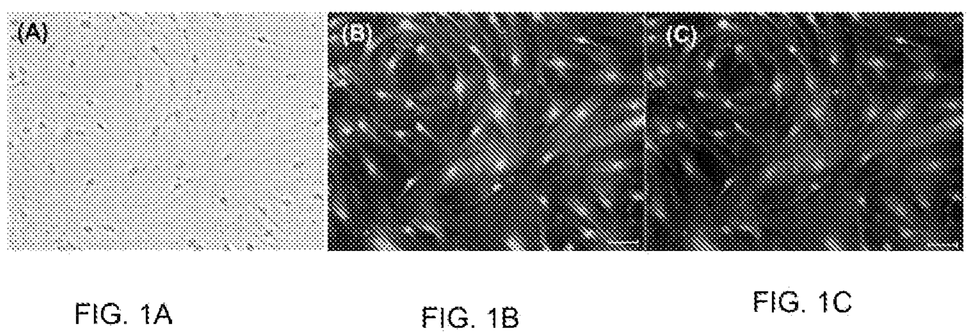
FIGS. 1A-1C depict microscopic characterization of isolated rabbit smooth muscle cells, (scale bar 20 μm).

In order for the present disclosure to be more readily understood, certain terms are first defined below. Additional definitions for the following terms and other terms are set forth throughout the specification.

As used herein, the terms "about" and "approximately" are used as equivalents. Any numerals used in this application with or without about/approximately are meant to cover any normal fluctuations appreciated by one of ordinary skill in the relevant art. In certain embodiments, the term "approximately" or "about" refers to a range of values that fall within 25%, 20%, 19%, 18%, 17%, 16%, 15%, 14%, 13%, 12%, 11%, 10%, 9%, 8%, 7%, 6%, 5%, 4%, 3%, 2%, 1%, or less in either direction (greater than or less than) of the stated reference value unless otherwise stated or otherwise evident from the context (except where such number would exceed 100% of a possible value).

As used herein, unless otherwise clear from context, the term "a" may be understood to mean "at least one." As used in this application, the term "or" may be understood to mean "and/or." In this application, the terms "comprising" and "including" may be understood to encompass itemized components or steps whether presented by themselves or together with one or more additional components or steps.

"Administration": As used herein, the term "administration" refers to the administration of a composition to a subject. Administration may be by any appropriate route. For example, in some embodiments, administration may be bronchial (including by bronchial instillation), buccal, enteral, interdermal, intra-arterial, intradermal, intragastric, intramedullary, intramuscular, intranasal, intraperitoneal, intrathecal, intravenous, intraventricular, mucosal, nasal, oral, rectal, subcutaneous, sublingual, topical, tracheal (including by intratracheal instillation), transdermal, vaginal and vitreal.

"Agent": As used herein, the term "agent" may refer to a compound or entity of any chemical class including, for example, polypeptides, nucleic acids, saccharides, lipids, small molecules, metals, or combinations thereof. As will be clear from context, in some embodiments, an agent can be or comprise a cell or organism, or a fraction, extract, or component thereof. In some embodiments, an agent is agent is or comprises a natural product in that it is found in and/or is obtained from nature. In some embodiments, an agent is or comprises one or more entities that is man-made in that it is designed, engineered, and/or produced through action of the hand of man and/or is not found in nature. In some embodiments, an agent may be utilized in isolated or pure form; in some embodiments, an agent may be utilized in crude form. In some embodiments, potential agents are provided as collections or libraries, for example that may be screened to identify or characterize active agents within them. Some particular embodiments of agents that may be utilized in accordance with the present disclosure include small molecules, antibodies, antibody fragments, aptamers, siRNAs, shRNAs, DNA/RNA hybrids, antisense oligonucleotides, ribozymes, peptides, peptide mimetics, small molecules, etc. In some embodiments, an agent is or comprises a polymer. In some embodiments, an agent is not a polymer and/or is substantially free of any polymer. In some embodiments, an agent contains at least one polymeric moiety. In some embodiments, an agent lacks or is substantially free of any polymeric moiety.

"Associated" or "Associated with": As used herein, the term "associated" or "associated with" typically refers to two or more entities in physical proximity with one another, either directly or indirectly (e.g., via one or more additional entities that serve as a linking agent), to form a structure that is sufficiently stable so that the entities remain in physical proximity under relevant conditions, e.g., physiological conditions. In some embodiments, associated entities are covalently linked to one another. In some embodiments, associated entities are non-covalently linked. In some embodiments, associated entities are linked to one another by specific non-covalent interactions (i.e., by interactions between interacting ligands that discriminate between their interaction partner and other entities present in the context of use, such as, for example, streptavidin/avidin interactions, antibody/antigen interactions, etc.). Alternatively or additionally, a sufficient number of weaker non-covalent interactions can provide sufficient stability for moieties to remain associated. Exemplary non-covalent interactions include, but are not limited to, affinity interactions, metal coordination, physical adsorption, host-guest interactions, hydrophobic interactions, pi stacking interactions, hydrogen bonding interactions, van der Waals interactions, magnetic interactions, electrostatic interactions, dipole-dipole interactions, etc.

"Differentiation": As used herein, the term "differentiation" refers to a change that occurs in cells to cause those cells to assume certain specialized functions and to lose the ability to change into certain other specialized functional units. Cells capable of differentiation may be any of totipotent, pluripotent or multipotent cells. Differentiation may be partial or complete with respect to mature adult cells.

"in vitro": As used herein, the term "in vitro" refers to events that occur in an artificial environment, e.g., in a test tube or reaction vessel, in cell culture, etc., rather than within a multi-cellular organism.

"in vivo": As used herein, the term "in vivo" refers to events that occur within a multi-cellular organism, such as a human and a non-human animal. In the context of cell-based systems, the term may be used to refer to events that occur within a living cell (as opposed to, for example, in vitro systems).

"Mold": As used herein, the term "mold" is intended to encompass any culture plate or substrate suitable for receiving, without limitation, at least one layer of smooth muscle cells and at least one other layer of neural progenitor cells, and guiding their integration into a circular construct. In certain embodiment, the mold can be a plate with a central post.

"Physiological conditions": As used herein, the phrase "physiological conditions", relates to the range of chemical (e.g., pH, ionic strength) and biochemical (e.g., enzyme concentrations) conditions likely to be encountered in the intracellular and extracellular fluids of tissues. For most tissues, the physiological pH ranges from about 6.8 to about 8.0 and a temperature range of about 20-40 degrees Celsius, about 25-40° C., about 30-40° C., about 35-40° C., about 37° C., atmospheric pressure of about 1. In some embodiments, physiological conditions utilize or include an aqueous environment (e.g., water, saline, Ringers solution, or other buffered solution); in some such embodiments, the aqueous environment is or comprises a phosphate buffered solution (e.g., phosphate-buffered saline).

"Substantially": As used herein, the term "substantially", and grammatic equivalents, refer to the qualitative condition of exhibiting total or near-total extent or degree of a characteristic or property of interest. One of ordinary skill in the art will understand that biological and chemical phenomena rarely, if ever, go to completion and/or proceed to completeness or achieve or avoid an absolute result.

"Subject": As used herein, the term "subject" refers to any living organism, including, but not limited to, humans, nonhuman primates such as chimpanzees and other apes and monkey species; farm animals such as cattle, sheep, pigs, goats, and horses; domestic mammals such as dogs and cats; laboratory animals including rodents such as mice, rats, rabbits and guinea pigs, and the like. The term does not denote a particular age or sex.

"Treating": As used herein, the term "treating" refers to partially or completely alleviating, ameliorating, relieving, inhibiting, preventing (for at least a period of time), delaying onset of, reducing severity of, reducing frequency of and/or reducing incidence of one or more symptoms or features of a particular disease, disorder, and/or condition. In some embodiments, treatment may be administered to a subject who does not exhibit symptoms, signs, or characteristics of a disease and/or exhibits only early symptoms, signs, and/or characteristics of the disease, for example for the purpose of decreasing the risk of developing pathology associated with the disease. In some embodiments, treatment may be administered after development of one or more symptoms, signs, and/or characteristics of the disease. In some embodiments, treatment may be administered as part of an intervention after development of one or more symptoms, signs, and/or characteristics of the disease.

It will be appreciated that for clarity, the following discussion will explicate various aspects of embodiments of the applicant's teachings, while omitting certain specific details wherever convenient or appropriate to do so. For example, discussion of like or analogous features in alternative embodiments may be somewhat abbreviated. Well-known ideas or concepts may also for brevity not be discussed in any great detail. The skilled person will recognize that some embodiments of the applicant's teachings may not require certain of the specifically described details in every implementation, which are set forth herein only to provide a thorough understanding of the embodiments. Similarly it will be apparent that the described embodiments may be susceptible to alteration or variation according to common general knowledge without departing from the scope of the disclosure. The following detailed description of embodiments is not to be regarded as limiting the scope of the applicant's teachings in any manner.

Fecal incontinence is generally the inability to control bowel movements. Stool (feces) unexpectedly leaks from the rectum. Symptoms of fecal incontinence (particularly related to the loss of control) can range from mild and occasional to frequent and severe. Causes of fecal incontinence can include, for example, trauma, such as giving birth or could be associate with aging. A non-functioning internal anal sphincter could be from muscle damage, making it difficult to hold stool back or could be from nerve damage, making it difficult to sense stool in the rectum or some combination thereof.

An injury to the perineum may result in a complete or partial destruction of the anal sphincter and the distal rectum. Such damage could potentially result in persistent incontinence or the need for permanent colostomy. Anorectal continence is maintained by interplay between the enteric nervous system, smooth muscle internal anal sphincter, the striated external anal sphincter and puborectalis muscles. The internal anal sphincter contributes >70% of the basal tension required to maintain continence. Damage to the integrity of the anorectum can result in fecal incontinence.

Additionally, loss of internal anal sphincter integrity and function can be a result of aging, anorectal surgery, and/or medical comorbidity. Again, these causes alone or collectively can lead in the treatment of fecal incontinence. The resulting psychological stress, social stigma, decreased self-esteem and productivity can be overwhelming. Overall, treatment strategies for fecal incontinence remain limited.

Current treatments for fecal incontinence are not optimal. Treatments include biofeedback, sacral nerve stimulation, myoblast injections, bulking agents, and artificial anal sphincter implantations. These technologies focus either on reinstatement of the striated muscle of the external anal sphincter or mechanical closure using artificial devices, with little focus on the reinstatement or preservation of terminal gut function. Terminal gut function requires coordinated contraction and relaxation of the smooth muscle of the rectum and internal anal sphincter mediated by the enteric nervous system.

The present disclosure encompasses a recognition that there is a need for implantable internal anal sphincter constructs that are capable of reestablishing function to the internal anal sphincter of a subject and methods of forming such constructs. In particular, the present disclosure encompasses a recognition that there is a need for such implantable internal anal sphincter constructs in subjects in which other standard therapies have already been tried and failed.

The present disclosure also encompasses a recognition that restoring internal anal sphincter function can include aspects of both muscle and nerve. Methods of the present disclosure include using cellular components, including smooth muscle and intrinsic neural components for engineering, regenerating, and/or reinstating healthy tissues and/or treating fecal incontinence. In some embodiments, constructs as provided herein are capable of reestablishing function to the internal anal sphincter of a subject in need thereof. In some embodiments, the present disclosure provides methods of forming such constructs.

Among other things, in some embodiments, the present disclosure provides internal anal sphincters and methods of fabricating and using these. In some embodiments, the present disclosure further provides methods of fabricating, forming, and/or generating such internal anal sphincter constructs. In some embodiments, the present disclosure provides methods for treating fecal incontinence using an internal anal sphincter construct to reinstate function.

Bioengineering Internal Anal Sphincters

In some embodiments, methods can include generating bioengineered internal anal sphincters by fabricating them using autologous neural progenitor cells and smooth muscle cells.

In some embodiments, provided methods can include autologous circular smooth muscle cells isolated from human internal anal sphincter and autologous enteric neurospheres (neural progenitor cells) isolated from human small intestine (jejunum). In some embodiments, the present disclosure provides methods of preparing and taking a biopsy of neural progenitor cells. In some embodiments, the present disclosure provides methods of preparing and taking a biopsy of smooth muscle cells. In some embodiments, provided methods can include preparing and taking a biopsy via a laparoscopic procedure.

In some embodiments, the present disclosure provides neural progenitor cells isolated from tissues of the small intestine. In some embodiments, the present disclosure provides smooth muscle cells isolated from tissues of anorectum. In some embodiments, the present disclosure provides a gel including neural progenitor cells isolated from tissues of the small intestine. In some embodiments, the present disclosure provides a bioengineer internal anal sphincter constructs.

In some embodiments, methods can include steps of seeding a dual layer gel matrix. In some embodiments, such a dual layer gel matrix can include a first gel layer of isolated smooth muscle cells and a second gel layer of isolated neural progenitor cells. In some embodiments, the layers of the matrix come in contact with one another on a culture plate where they are seeded in a circular shape. In some embodiments, the circular shaped is to approximate the shape of an internal anal sphincter. In some embodiments, methods can include contacting the dual layer gel with a differentiation media to form circular, intrinsically innervated internal anal sphincter constructs of directionally oriented smooth muscle cells.

In some embodiments, these bioengineered internal anal sphincter constructs are useful for implantation in a subject. In some embodiments, at least one of these constructs is useful as an implant in the treatment of fecal incontinence. In some embodiments, a plurality of these constructs, for example, more than one, is useful as an implant in the treatment of fecal incontinence. In some embodiments, at least two of these constructs in conjunction are useful in an implant in the treatment of fecal incontinence. In some embodiments, at least three of these constructs in conjunction are useful in an implant in the treatment of fecal incontinence. In some embodiments, at least four of these constructs in conjunction are useful in an implant in the treatment of fecal incontinence. In some embodiments, at least five or more of these constructs in conjunction are useful in an implant in the treatment of fecal incontinence.

Biopsying a Subject's Tissue

In some embodiments, methods of generating an internal anal sphincter construct can include steps of obtaining an anorectum tissue cell biopsy from a subject. In some embodiments, methods can include obtaining a biopsy from the subject's internal anal sphincter tissue. In some embodiments, the step of obtaining the anorectum tissue cell biopsy and/or the internal anal sphincter tissue biopsy can be performed laparoscopically.

In some embodiments, methods of generating an internal anal sphincter construct can include steps of obtaining an intestinal tissue cell biopsy from a subject. In some embodiments, methods can include obtaining a biopsy from the subject's jejunal small intestine tissue. In some embodiments, the step of obtaining the intestinal tissue cell biopsy and/or the jejunal small intestine tissue biopsy can be performed laparoscopically.

In some embodiments, two biopsies can be collected from the same subject. In some embodiments, biopsies of a subject's internal anal sphincter can be used for the smooth muscle samples. In some embodiments, biopsies of a subject's can be used to isolate the neural progenitor cells. In some embodiments, biopsies can be useful to construct bioengineered internal anal sphincter constructs as provided herein.

Isolating Cells

In some embodiments, methods can include isolating neural progenitor cells from a subject. In some embodiments, a source of autologous neural progenitor cells as taught by the present disclosure can include tissue from a subject's small intestine. In some embodiments, the neural progenitor cells can be taken from a biopsy of a subject's small intestine. In some embodiments, the small intestine biopsy can be a laparoscopic procedure and/or operation. In some embodiments, a small intestine biopsy can include a longitudinal intestinal biopsy on an antimesenteric side of the jejunum.

In some embodiments, methods can include isolating smooth muscle cells from a subject. In some embodiments, a source of autologous smooth muscle cells as taught by the present disclosure includes anorectum tissue and/or internal anal sphincter tissue. In some embodiments, a biopsy will be taken of an internal anal sphincter. In some embodiments, the biopsy can be sharply taken with scissors. In some embodiments, jejunal biopsy tissue can be removed from the subject's abdominal cavity and passed off the surgical field in a sterile fashion.

In some embodiments, a first biopsy from the small intestinal tissue can be obtained laparoscopically and provides autologous neural progenitor cells for a subject's internal anal sphincter construct. In some embodiments, a biopsy sample is about 25 mg; about 50 mg; about 75 mg; about 100 mg; about 150 mg; about 175 mg; about 200 mg; about 250 mg; about 300 mg; about 350 mg; about 400 mg; about 450 mg; about 500 mg; or more.

In some embodiments, a second biopsy from the internal anal sphincter can be obtained through surgical retrieval and provides autologous smooth muscle cells for a subject's internal anal sphincter construct. In some embodiments, a biopsy sample is about 25 mg; about 50 mg; about 75 mg; about 100 mg; about 150 mg; about 175 mg; about 200 mg; about 250 mg; about 300 mg; about 350 mg; about 400 mg; about 450 mg; about 500 mg; or more.

In some embodiments, internal anal sphincter and jejunal biopsy specimens from the subject can be delivered for tissue preparation, culture, and expansion of both smooth muscle cells and neural progenitor cells. In some embodiments, biopsied tissues, including a small intestine biopsy and an anorectum tissue biopsy can undergo separate processing. In some embodiments, smooth muscle cells and neural progenitor cells will be used to bioengineer internal anal sphincter constructs as provided herein. In some embodiments, provided internal anal sphincter constructs are useful for implantation in accordance with methods as provided herein.

In some embodiments, while not wishing to be bound to a theory, it is believed that because the bioengineered internal anal sphincter constructs can be fabricated from a subject's cells, there is a reduced likelihood of an immunologic response and/or rejection in a subject following implantation. In some embodiments, there is minimal to no immunologic response or rejection in a subject due to implantation of provided internal anal sphincter constructs.

Mechanically Dissecting and Enzymatically Digesting Neural Progenitor Cells

In some embodiments, processing of a small intestine biopsy can include steps of washing the biopsy with an antibiotic solution. In some embodiments, washing can include a washing cycle, which can include shaking at about 5 rpm; about 10 rpm; about 50 rpm; about 100 rpm; about 250 rpm; about 500 rpm or about 1000 rpm or more. In some embodiments, the washing cycle can extend for about 5 min; about 10 min; about 15 min; about 20 min; about 25 min; about 30 min; about 35 min; about 40 min; about 45 min; about 50 min; about 55 min; about 60 min; about 2 hours; or about 3 hours; or more. In some embodiments, washing can include a plurality of washing cycles, for example, two cycles, three cycles, four cycles, or more. In some embodiments, the antibiotic solution can include, for example, HBSS with 240 μg/ml Gentamicin, 160 μg/ml Vancomycin, 500 μg/ml Ceftazidime, 5.4 μg/ml Amphotericin B and 200 μg/ml Amikacin. In some embodiments, the antibiotic solution can include, for example, HBSS containing 2× antibiotic/antimycotic (200 U/ml Penicillin G, 200 μg/ml Streptomycin and 0.5 μg/ml Amphotericin B) and 50 μg/ml Gentamicin.

In some embodiments, processing of washed biopsied tissues can include mincing of the tissues into fine pieces. In some embodiments, processing can include centrifuging the pieces in a disinfecting solution. In some embodiments, processing further includes steps of enzymatically digesting the pieces in an enzyme solution. In some embodiments, the enzyme solution, includes a collagenase and another protease, for example, 18.5 μl/ml Collagenase HA and 26.1 μl/ml BP protease. In other embodiments, the enzyme solution, includes, for example, a collagenase, e.g., a type II collagenase and a neutral protease, e.g., Dispase II. In some embodiments, the enzymatic digestion includes shaking and/or mixing. In some embodiments, the shaking and/or mixing can occur for about 30 minutes; about 45 min; about 60 min; about 2 hours; about 3 hours; about 4 hours; about 5 hours; about 6 hours; about 7 hours; about 8 hours; about 9 hours; about 10 hours; or more. In some embodiments, the shaking and/or mixing can occur at about 5 rpm; about 10 rpm; about 50 rpm; about 100 rpm; about 250 rpm; about 500 rpm or about 1000 rpm or more.

In some embodiments, processing can further include centrifuging the digested tissue. In some embodiments, processing further includes steps of enzymatically digesting the centrifuged supernatant in a second enzymatic digest, which can include 18.5 μl/ml collagenase HA and 26.1 μl/ml BP protease. In some embodiments, the enzymatic digestion includes shaking and/or mixing. In some embodiments, the enzymatic digestion includes shaking and/or mixing. In some embodiments, the shaking and/or mixing can occur for about 30 minutes; about 45 min; about 60 min; about 2 hours; about 3 hours; about 4 hours; about 5 hours; about 6 hours; about 7 hours; about 8 hours; about 9 hours; about 10 hours; or more. In some embodiments, the shaking and/or mixing can occur at about 5 rpm; about 10 rpm; about 50 rpm; about 100 rpm; about 250 rpm; about 500 rpm or about 1000 rpm or more. In some embodiments, processing further includes centrifuging the digested tissue and suspending the pelleted tissue in a neural growth media. In some embodiments, the neural growth media can include, for example, Phenol Red Free Neural Basal A Medium (ThermoFisher) or a Neurobasal media (Invitrogen) supplemented with 1% N2 supplement, 20 ng/ml bFGF, 20 ng/ml EGF, 1 mM L-Glutamine and 1× antibiotic/antimycotic.

Mechanically Dissecting and Enzymatically Digesting Smooth Muscle Cells

In some embodiments, processing an internal anal sphincter biopsy can include washing the tissue in an antibiotic solution. In some embodiments, washing can include a washing cycle, which can include shaking at about 5 rpm; about 10 rpm; about 50 rpm; about 100 rpm; about 250 rpm; about 500 rpm or about 1000 rpm or more. In some embodiments, the washing cycle can extend for about 5 min; about 10 min; about 15 min; about 20 min; about 25 min; about 30 min; about 35 min; about 40 min; about 45 min; about 50 min; about 55 min; about 60 min; about 2 hours; or about 3 hours; or more. In some embodiments, washing can include a plurality of washing cycles, for example, two cycles, three cycles, four cycles, or more. In some embodiments, the antibiotic solution can include HBSS with 240 μg/ml Gentamicin, 160 μg/ml Vancomycin, 500 μg/ml Ceftazidime, 5.4 μg/ml Amphotericin B and 200 μg/ml Amikacin. In some embodiments, the antibiotic solution can include HBSS containing 2× antibiotic/antimycotic (200 U/ml Penicillin G, 200 μg/ml Streptomycin and 0.5 μg/ml Amphotericin B) and 50 μg/ml Gentamicin.

In some embodiments, processing of washed biopsied tissues can include mincing of the tissues into fine pieces. In some embodiments, processing can include centrifuging the pieces in a disinfecting solution. In some embodiments, processing further includes steps of enzymatically digesting the pieces in an enzyme solution. In some embodiments, the enzyme solution, includes, for example, 1 mg/ml collagenase DE. In some embodiments, the enzymatic digestion includes shaking and/or mixing. In some embodiments, the shaking and/or mixing can occur for about 30 minutes; about 45 min; about 60 min; about 2 hours; about 3 hours; about 4 hours; about 5 hours; about 6 hours; about 7 hours; about 8 hours; about 9 hours; about 10 hours; or more. In some embodiments, the shaking and/or mixing can occur at about 5 rpm; about 10 rpm; about 50 rpm; about 100 rpm; about 250 rpm; about 500 rpm or about 1000 rpm or more.

In some embodiments, processing can further include centrifuging the digested tissue. In some embodiments, processing further includes steps of enzymatically digesting the centrifuged supernatant in a second enzymatic digest, which can include 1 mg/ml collagenase DE. In some embodiments, the enzymatic digestion includes shaking and/or mixing. In some embodiments, the shaking and/or mixing can occur for about 30 minutes; about 45 min; about 60 min; about 2 hours; about 3 hours; about 4 hours; about 5 hours; about 6 hours; about 7 hours; about 8 hours; about 9 hours; about 10 hours; or more. In some embodiments, the shaking and/or mixing can occur at about 5 rpm; about 10 rpm; about 50 rpm; about 100 rpm; about 250 rpm; about 500 rpm or about 1000 rpm or more. In some embodiments, processing further includes centrifuging the digested tissue. In some embodiments, processing further includes a plurality of steps of centrifuging the digested tissue. In some embodiments, processing further includes centrifuging the digested tissue and suspending the pelleted tissue in a smooth muscle cell growth media. In some embodiments, the smooth muscle cell growth media can include Smooth muscle cell media consisted of DMEM high glucose (Invitrogen) supplemented with 10% FBS, 2.5 mM L-glutamine and 1× antibiotic/antimycotic.

Expanding and Harvesting Neural Progenitor Cells

In some embodiments, processes include monitoring neural progenitor cell counts. In some embodiments, steps include monitoring neural progenitor cells under a microscope for formation of cell clusters. In some embodiments, when cell cluster density reaches about 40%; about 50%; about 60%; about 70%; about 80%; or about 90%, steps further include centrifuging cells. In some embodiments, steps further include digesting the pellet, for example in Accutase, followed by steps of neutralizing in a media, for example Phenol Red Free Neural Basal A medium, Neuro Basal medium (Invitrogen) or Dulbecco's Modified Eagle Medium-F12 media. In some embodiments, processes further includes a step of cell counting. In some embodiments, steps are repeated until cell counts reach at least 250,000; at least 500,000; at least 1 million; at least 2 million; at least 2.5 million; at least 3 million; at least 3.5 million; at least 4 million; at least 4.5 million; at least 5 million; at least 7.5 million; at least 10 million; at least 15 million; at least 20 million; at least 25 million; at least 50 million; or more.

Expanding and Harvesting Smooth Muscle Cells

In some embodiments, processes include monitoring smooth muscle cell cultures, counts. In some embodiments, processes include monitoring smooth muscle cell counts. In some embodiments, when cells reach about 40%; about 50%; about 60%; about 70%; about 80%; or about 90%, confluence, steps further include harvesting smooth muscle cells, for example, using cell-dissociation enzymes, such as TrypeLE reagents. In some embodiments, harvesting releases the cells from the plate and sub-cultured to expand to the number of cells. In some embodiments, processes further includes a step of cell counting. In some embodiments, steps are repeated until cell counts reach at least 250,000; at least 500,000; at least 1 million; at least 2 million; at least 2.5 million; at least 3 million; at least 3.5 million; at least 4 million; at least 4.5 million; at least 5 million; at least 7.5 million; at least 10 million; at least 15 million; at least 20 million; at least 25 million; at least 50 million; or more.

Preparing a Silicone Plate and/or Mold

In some embodiments, the methods include a step of providing molds for bioengineering internal anal sphincters as disclosed herein. In some embodiments, the step of providing a mold can further include preparing a mold. In some embodiments, molds are formed from or fabricated from silicone, for example, medical grade silicone. In some embodiments, the step of forming a mold can include mixing an elastomer with a curing reagent, pouring the mixture on plates, and curing the plates. Additionally, the step of forming a mold can including lining a plate with a layer of silicone; preparing a silicone post; punching a post hole in the plate; and curing the silicone post in the post hole to fix the post to the plate thereby forming the mold. In some embodiments, the step of curing is a heating. In some embodiments, a step of curing is a UV exposure. In some embodiments, once molds are formed, steps further include sterilizing. In some embodiments, a mold's size can depend on a size of a construct to be fabricated. For example, in some embodiments, a mold can be characterized by its diameter and/or width. In some embodiments, for example, a diameter of a mold can be about 30 mm to about 100 mm. In some embodiments, a diameter of a mold can be about 30 mm; about 35 mm; about 40 mm; about 45 mm; about 50 mm; about 55 mm; about 60 mm; about 65 mm; about 70 mm; about 75 mm; about 80 mm; about 85 mm; about 90 mm; about 95 mm; or about 100 mm. In some embodiments, a mold can include a central post. For example, in some embodiments, a mold can be characterized by a diameter of the central post. In some embodiments, for example, a diameter of a central post of the mold can be about 5 mm to about 40 mm. In some embodiments, a diameter of a central post of the mold can be about 5 mm; about 8 mm; about 10 mm; about 12 mm; about 14 mm; about 16 mm; about 18 mm; about 20 mm; about 22 mm; about 24 mm; about 26 mm; about 28 mm; about 30 mm; about 32 mm; about 34 mm; about 36 mm; about 38 mm; or about 40 mm.

Co-Culturing

In some embodiments, methods can include steps of suspending the expanded culture of neural progenitor cells in a collagen/laminin gel. In some embodiments, methods can include suspending the expanded culture of neural progenitor cells in a gel mixture including medical grade collagen, recombinant laminin, Phenol Red Free Neural Basal A medium, Neuro Basal medium (Invitrogen) or Dulbecco's Modified Eagle Medium and water. In some embodiments, methods can include steps of laying the neural progenitor cells onto a prepared mold. In some embodiments, the step of laying the neural progenitor cells onto the prepared mold includes uniformly laying the neural progenitor cells on a plate of the mold. In some embodiments, the step of laying the neural progenitor cells onto the prepared mold includes laying the neural progenitor cells in a substantially circular shape on the plate. In some embodiments, the step of laying the neural progenitor cells onto the prepared mold include laying the neural progenitor cells around a central post of the mold. In some embodiments, steps include gently mixing the neural progenitor cells suspension. In some embodiments, methods can include steps of gelling the neural progenitor cells in the gel mixture. In some embodiments, methods can include steps of gently swirling the plates to ensure complete coverage of the plate and the mixture. In some embodiments, steps include gelling in an incubator until gelation is observed. In some embodiments, steps of gelling, for example, occur for around for at least 20 minutes at 37° C. and 7% $CO_2$.

In some embodiments, methods can include steps of suspending the smooth muscle cells in a collagen gel. In some embodiments, methods can include suspending the expanded culture of smooth muscle cells in a gel mixture including medical grade collagen, Smooth Muscle Cell Medium (Promocell) or Dulbecco's Modified Eagle Medium and water. In some embodiments, steps include layering the smooth muscle cell/collagen gel on the gel having the neural progenitor cells. In some embodiments, methods can include steps of gelling the smooth muscle cells. In some embodiments, the gelling, for example, occurs for around for at least 45 minutes at 37° C. and 5% $CO_2$.

Adding Differentiating Media and Forming Constructs

In some embodiments, following gelation, methods including adding differentiation media to the plate. In some embodiments, the smooth muscle cells contract both gels into a ring-like structure around the post to form an internal anal sphincter. In some embodiments, cell mixtures ultimately coalesce forming ring-like constructs around the central post. In some embodiments, constructs form within 48 hours. In some embodiments, constructs mature within 10-12 days. In some embodiments, differentiation media includes, for example, Neurobasal-A media (Invitrogen) supplemented with B27 supplement, 1% FBS and 1× antibiotic/antimycotic. In some embodiments, differentiation media includes, for example, Neurobasal-A media (Invitrogen) supplemented with 1% FBS and Gentamicin.

The following examples illustrate some embodiments and aspects of the present disclosure. It will be apparent to those skilled in the relevant art that various modifications, additions, substitutions, and the like can be performed without altering the spirit or scope of the disclosure, and such modifications and variations are encompassed within the scope of the disclosure as defined in the claims, which follow. The present disclosure will be more fully understood by reference to these examples. The following examples do not in any way limit the present disclosure or the claimed disclosures and they should not be construed as limiting the scope.

EXAMPLE 1

This example discloses obtaining biopsy samples from New Zealand white rabbits.

The anatomy of the New Zealand white rabbit and the surgical planes of the anal area are similar to humans. Nonclinical studies were conducted to test the safety and efficacy of using autologous cell bioengineered internal anal sphincter constructs as a regenerative medicine approach for treating induced fecal incontinence in rabbits. All animals underwent internal anal sphincter hemi-sphincterectomy to induce fecal incontinence. Fecal incontinence was assessed in each animal after sphincterectomy and compared to same before sphincterectomy by (1) regular observation of fecal hygiene and (2) regular anorectal manometry.

Anorectal manometry was performed as follows: a catheter with four circumferential sensors attached to an inflatable balloon was used to measure two parameters: anal basal pressure and rectoanal inhibitory reflex (RAIR). These two parameters were used as a measure for normal anorectum physiological functioning and fecal incontinence. Anal basal pressure is the highest identified pressure zone generated by the internal anal sphincter. RAIR is the ability of the internal anal sphincter to relax following inflation of the balloon. Baseline readings were obtained on all rabbits before any surgeries.

Following hemi-sphincterectomy, anorectal manometry was performed on all rabbits to confirm fecal incontinence, which was identified by lack of fecal hygiene and by significant decrease in anal basal pressure and RAIR in all rabbits. All rabbits were followed by anorectal manometry regularly until they reached their respective time points.

Rabbits were randomly divided into three experimental groups: 1) Non-treated group (Incontinent control), 2) Treated group (received surgical implantation of bioengineered internal anal sphincter constructs 6-8 weeks following sphincterectomy through a surgical opening of the anal verge), and 3) Sham surgery group (Surgical opening of the anal verge was performed followed by immediate closure without implantation of bioengineered internal anal sphincter constructs). Rabbits underwent hemi-sphincterectomy to induce fecal incontinence. Cells were used to bioengineer Sphincters in vitro. Rabbits were then randomly assigned to one of 3 groups (non-treated, treated and sham surgery groups). Anorectal Manometry was performed at regular intervals together with observation of fecal hygiene to assess the status of the animals' welfare. Table 1 shows post-implantation safety of bioengineered internal anal sphincter constructs in rabbits at three-time points (3, 6, and 12 months).

TABLE 1

Study Design for the Non-Clinical Rabbit Study.

| | Baseline manometry | Sphincterectomy to induce FI | Manometry post sphincterectomy | 4-6 weeks post sphincterectomy | 1 month | 3 months | 6 months | 12 months |
|---|---|---|---|---|---|---|---|---|
| Non-treated group | ✓ | ✓ | ✓ | No treatment | Manometry post sphinc-terectomy | Manometry post sphinc-terectomy | Manometry post sphinc-terectomy | Manometry post sphinc-terectomy |
| Treated group | ✓ | ✓ | ✓ | Implant bioengineered internal anal Sphincter constructs | Manometry post implant | Manometry post implant | Manometry post implant | Manometry post implant |

TABLE 1-continued

| Study Design for the Non-Clinical Rabbit Study. | | | | | | | | |
|---|---|---|---|---|---|---|---|---|
| | Baseline manometry | Sphincterectomy to induce FI | Manometry post sphincterectomy | 4-6 weeks post sphincterectomy | 1 month | 3 months | 6 months | 12 months |
| Sham surgery group | ✓ | ✓ | ✓ | Sham surgery | Manometry post sham | Manometry post sham | Manometry post sham | Manometry post sham |

A total of 26 rabbits were included in the study. Eleven rabbits were in the non-treated group (1 sacrificed at 3 months, 5 sacrificed at 6 months, and 5 sacrificed at 12 months). Ten rabbits were included in the treated group (3 sacrificed at 3 months and 7 sacrificed at 12 months). Five rabbits were included in the sham surgery group, all of them sacrificed at 12 months. Anorectal manometry was performed at regular intervals on all animals in the study. In the non-treated group, 1 animal was sacrificed at 3 months, 5 animals were sacrificed at 6 months, and 5 animals were sacrificed at 12 months. In the Treated group, 3 animals were sacrificed at 3 months and 7 animals were sacrificed at 12 months. In the Sham surgery group, 5 animals were sacrificed at 12 months.

The design of the study is summarized in below Table 2.

TABLE 2

| Time Points for Study Design | | | | |
|---|---|---|---|---|
| | Sacrifice time points | | | |
| | 3 mo | 6 mo | 12 mo | Total |
| Non-treated group: internal anal sphincter hemi-sphincterectomy followed by no treatment | 1 | 5 | 5 | 11 |
| Treated group: internal anal sphincter hemi-sphincterectomy followed by implantation of bioengineered internal anal sphincter constructs | 3 | | 7 | 10 |
| Sham surgery group: internal anal sphincter hemi-sphincterectomy followed by sham procedure | | | 5 | 5 |

All the rabbits were six months old at the beginning of enrolment. The average weight of the rabbits was 2.9±0.2 kg, at the beginning of enrolment. Each animal was given a unique identification that was maintained throughout the study. Animals were acclimated for at least six days prior to enrollment in the study. Animals were examined and approved for use by a staff veterinarian prior to inclusion in the study.

Collecting the Rabbit Small Intestine Biopsy

Before internal anal sphincter hemi-sphincterectomy surgery, on the same day, rabbits underwent small intestinal biopsy. A midline laparotomy was made through the abdominal wall fascia. Two sections separated by 10 cm were identified in the small intestine. An antimesenteric biopsy was taken sharply and then immediately placed in 2-8° C. HBSS transport medium (Hank's balanced salt solution (HBSS) with 50 μg/ml mlgentamicin), passed off the field for culture. Two full thickness intestinal biopsies (total up to 0.07±0.03 g; n=21) were obtained. The antimesenteric defects were closed with a running 5-0 PDS suture. The closure was leak tested by applying manual pressure at the proximal and distal ends of the closure. Suture line disruptions were reinforced with 5-0 PDS suture in an interrupted fashion. The peritoneal cavity was then irrigated and closed with a running suture on the fascia and interrupted skin closure.

Collecting the Rabbit Internal Anal Sphincter Biopsy

Following the small intestine biopsy, the internal anal sphincter area was prepped and draped in the standard surgical fashion. A ventral hemi-circumferential, curvilinear incision was made through the anocutaneous tissue using a #11 blade scalpel. The dissection was carried more proximally to identify the tissue plane between the anal canal submucosa and internal anal sphincter. This plane was identified throughout the length of the hemi-circumferential incision. The internal anal sphincter was then dissected from the submucosal plane and the overlying external anal sphincter for 1 cm. The internal anal sphincter fibers were then sharply amputated. A total of up to 0.11±0.04 g; n=21 of internal anal sphincter tissue was obtained. Internal anal sphincter tissue was then immediately placed in 2-8° C. HBSS transport medium (Hank's balanced salt solution (HBSS) with 50 μg/ml gentamicin). Once the internal anal sphincter had been circumferentially amputated, the incision was closed with interrupted 4-0 Prolene suture.

EXAMPLE 2

This example discloses isolating smooth muscle cells and neural progenitor cells from biopsy samples.

Neural Progenitor Cells

The intestinal biopsies were washed extensively with HBSS containing 2× antibiotic/antimycotic (200 U/ml Penicillin G, 200 μg/ml Streptomycin and 0.5 μg/ml Amphotericin B) and 50 μg/ml Gentamicin. The tissue was minced, washed, and subjected to digestion twice in a mixture containing mixed proteases, e.g., type II Collagenase and Dispase II. The cells were recovered by centrifugation and washed before being passed through a 70 μm nylon cell strainer. Cells were washed and re-suspended in neural growth medium before being filtered through a 40 μm nylon cell strainer. Neural progenitor cells can be plated in neural growth media including Phenol Red Free Neural Basal A Medium (ThermoFisher) or a Neurobasal media (Invitrogen), optionally supplemented with 1% N2 supplement, 20 ng/ml bFGF, 20 ng/ml EGF, 1 mM L-Glutamine and 1× antibiotic/antimycotic. Under these culture conditions, single cells aggregated, replicated, and formed enteric neural progenitor cells at 37° C. under 7% $CO_2$. A sample of the cells was taken for characterization.

Smooth Muscle Cells

Internal anal sphincter tissue excised from the rabbit was rapidly cleaned in ice-cold carbonated HBSS containing 2× antibiotic/antimycotic (200 U/ml Penicillin G, 200 μg/ml Streptomycin and 0.5 μg/ml Amphotericin B) and 50 μg/ml Gentamicin. The tissue was finely minced and digested twice using a collagenase, such as Collagenase type II for 1 hour each digest. The cells were collected, washed, and re-suspended in growth medium before plating onto tissue culture flasks at 37° C. under 5% $CO_2$. Smooth muscle cell media consisted of DMEM high glucose (Invitrogen) supplemented with 10% FBS, 2.5 mM L-glutamine and 1× antibiotic/antimycotic. A sample of the cells was taken for characterization.

Both cell types were expanded for 4 weeks to obtain the required number to form the bioengineered internal anal sphincter complexes.

EXAMPLE 3

The present example characterizes of isolated rabbit smooth muscle cells and isolated rabbit neural progenitor cells from biopsy samples.

Isolated autologous internal anal sphincter smooth muscle cells and small intestine neural progenitor cells obtained from rabbits were characterized for identification before using for final bioengineered internal anal sphincter construct.

Smooth Muscle Cells

Autologous smooth muscle cells isolated from rabbit internal anal sphincter biopsy were allowed to grow in culture. As shown in FIGS. 1A-1C, the identity of smooth muscle cells was confirmed by observing their spindle-like morphology under microscope. Smooth muscle cells were grown on coverslips for immunofluorescence studies. Smooth muscle cells were stained with smooth muscle markers; α-smooth muscle actin and smoothelin. Cells stained positive confirming contractile phenotype of smooth muscle cells. FIG. 1A shows smooth muscle cells that were grown in a culture and acquired their normal spindle like morphology. Smooth muscle cells stained positive for α-smooth muscle actin are shown in FIG. 1B while FIG. 1C shows cells expressing smoothelin, a smooth muscle specific marker indicating that the cells acquired their mature phenotype.

Figure 2:
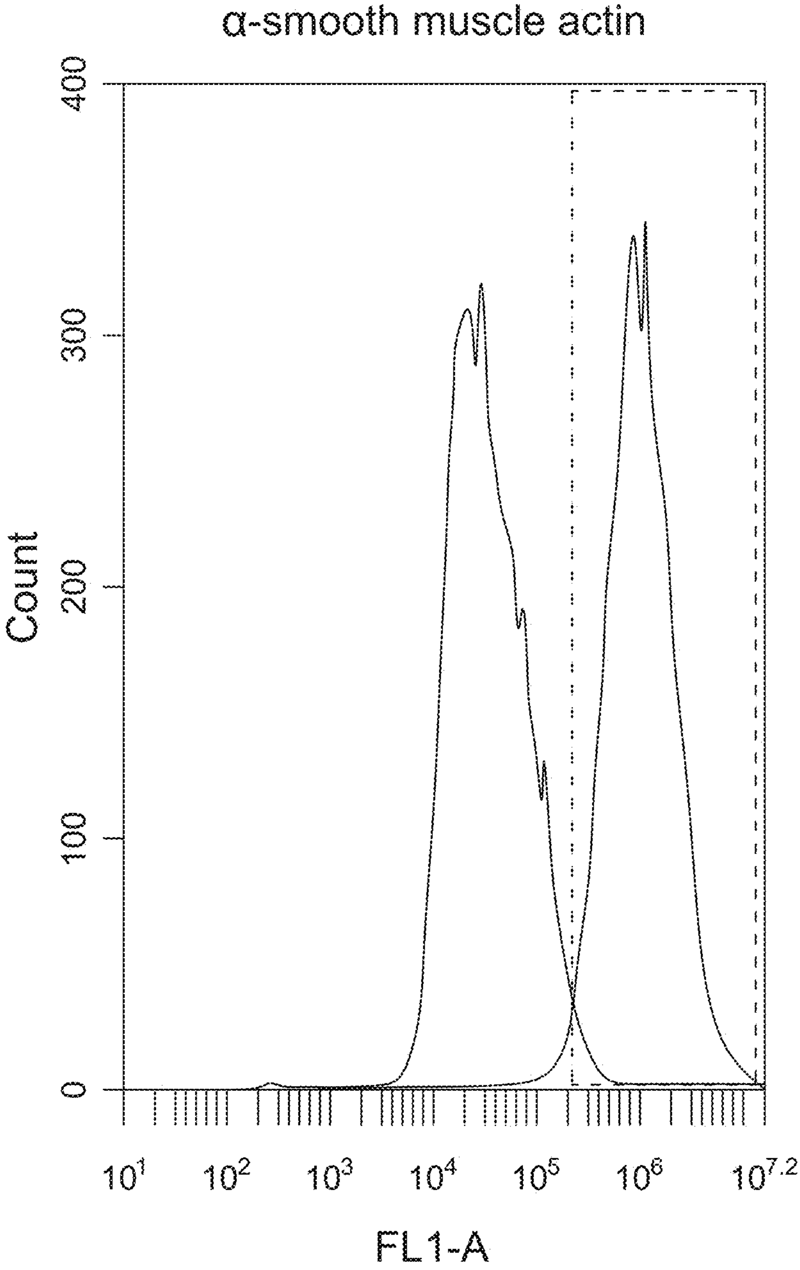
FIG. 2 depicts exemplary flow cytometry analysis of isolated rabbit internal anal sphincter smooth muscle cells.

Additionally, the phenotype of the isolated smooth muscle cells was characterized by flow cytometry. α-smooth muscle actin was used as an indicator for smooth muscle specificity. Cultured internal anal sphincter smooth muscle cells were incubated with primary α-smooth muscle actin antibody followed by incubation with appropriately conjugated fluorescent secondary antibody. Unstained cells and cells stained with secondary antibody only were used as controls. Flow cytometry data analysis showed that over 94.5±4.5% (n=3) of the isolated internal anal sphincter smooth muscle cells expressed α-smooth muscle actin. A graphical representation of the flow cytometry analysis of isolated rabbit internal anal sphincter smooth muscle cells is depicted in FIG. 2. Isolated internal anal sphincter smooth muscle cells were expanded and analyzed by flow cytometry for expression of smooth muscle marker α-smooth muscle actin. Flow data showed that over 94.5% of the cell population expressed α-smooth muscle actin (in the red box) as compared to cells stained with secondary antibody only (peak to the left of the red box). This indicated a high proportion of smooth muscle cells in the culture.

Neural Progenitor Cells

Figures 3A, 3B, 3C, 3D, 3E, 3F:
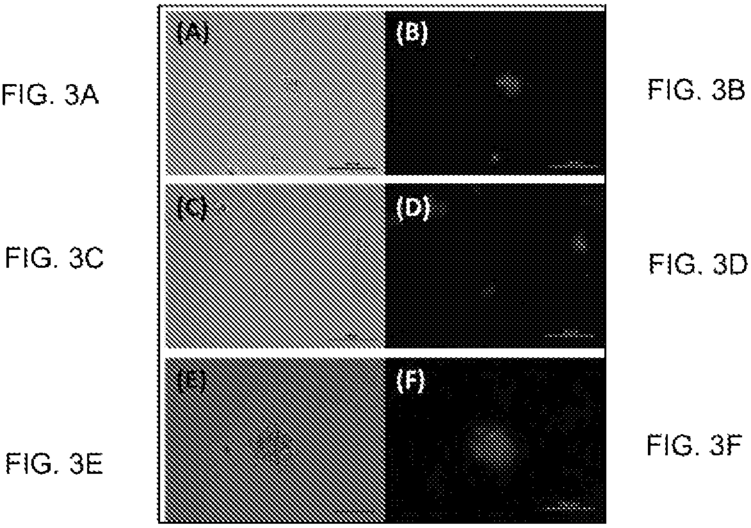
FIGS. 3A-3F provides microphotographic characterization of isolated rabbit neural progenitor cells positive stained for neural stem cell markers (scale bar 100 μm).

Autologous neural progenitor cells isolated from rabbit small intestine were visualized under the microscope. Cells clustered into small floating bodies called neurospheres. Cells were then characterized by immunofluorescence and stained positive for $p75^{NTR}$, Nestin and Sox2, confirming neural crest-derived stem cells. (NTR is a neurotrophin receptor). FIG. 3 depicts the microscopic characterization of these isolated neural progenitor cells. The neural progenitor cells isolated from the small intestine of rabbits formed neurospheres. As shown in the bright-field images FIGS. 3A, 3C, and 3E. Positive staining for neural stem cell markers $p75^{NTR}$, Sox2, and Nestin was demonstrated in the neurospheres as shown in FIGS. 3B, 3D and 3F, respectively, (scale bar 100 μm);

EXAMPLE 4

The present example discloses forming a bioengineered rabbit internal anal sphincter construct in accordance with the present disclosure.

Figure 4:
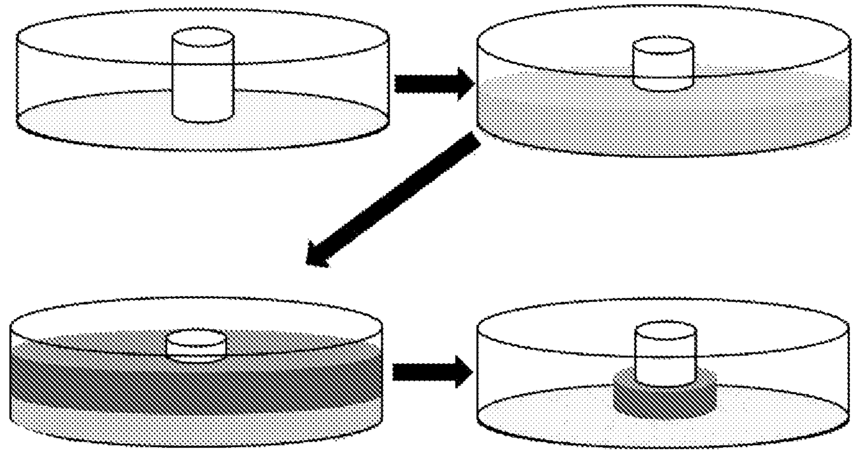
FIG. 4 depicts a schematic representation of a process of bioengineering an internal anal sphincter construct in accordance with some embodiments of the present disclosure. The empty mold is illustrated at the upper left portion of FIG. 4. The first step as illustrated in the upper right portion of FIG. 4 shows neural progenitor cells suspended in a dish or mold. In the second step illustrated at the lower left shows smooth muscle cells suspended on top of the first gel layer. The lower right portion of the figure shows the mixtures having coalesced and formed ring-like constructs in accordance with various embodiments.

The design of the engineering process is depicted in FIG. 4. FIG. 4 at panel (A) shows neural progenitor cells were suspended in a type I collagen/laminin mixture and plated onto a silicone-coated 35 mm petri dish with an 8-mm diameter central post. The mixture was placed into a 37° C. humidified incubator and allowed to gel. FIG. 4 at panel (B) shows a second mixture containing internal anal sphincter smooth muscle cells suspended in type I collagen was added on top of the first gel layer. FIG. 4 at panel (C), following gelation of the second hydrogel layer, differentiation media was added and then regularly changed every other day up to 12 days. Mixtures coalesced and formed ring-like structures around the central post within 48 hours.

EXAMPLE 5

The present example characterizes bioengineered internal anal sphincter constructs formed in accordance with methods disclosed herein.

Histology, Hematoxylin and Eosin (H&E) Staining and Immunostaining

Figure 5:
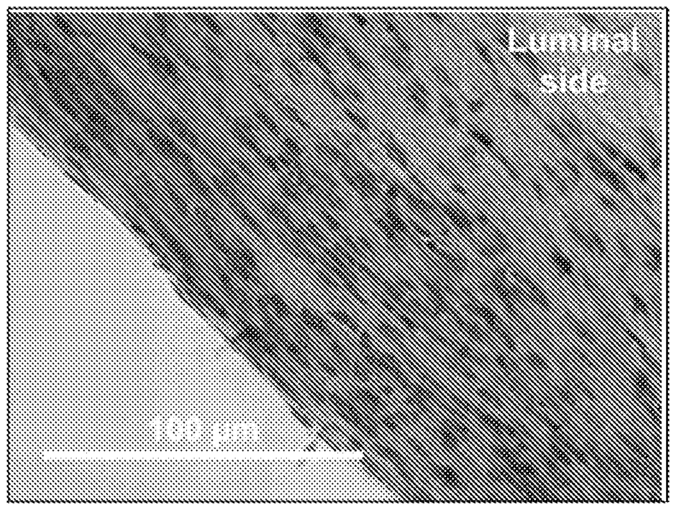
FIG. 5 depicts exemplary hematoxylin and eosin staining of a bioengineered internal anal sphincter construct.

Rabbit bioengineered internal anal sphincter constructs were stained with specific markers to check the presence and distribution of differentiated cells. Bioengineered internal anal sphincter constructs were fixed and embedded in paraffin. Cross sections were obtained and stained with H&E. The presence of aligned smooth muscle cells was confirmed by positive H&E stain. FIG. 5 depicts the stain showing the circumferential alignment of the smooth muscle cells around the luminal side (i.e. located near the central post) in the bioengineered internal anal sphincter construct.

Figures 6A, 6B:
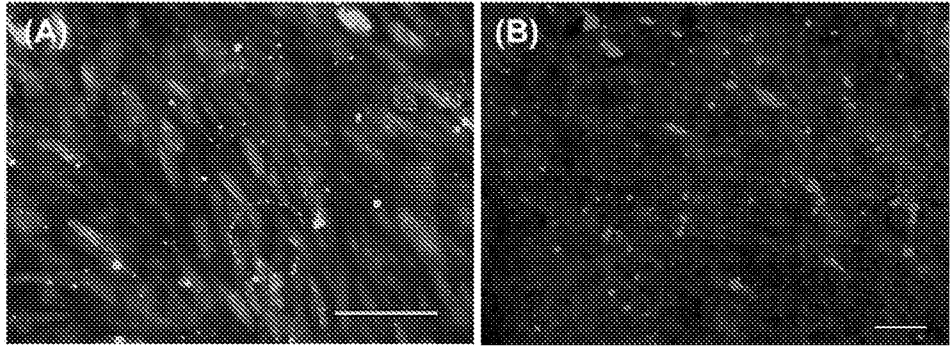
FIGS. 6A-6B depict immunohistochemistry of a bioengineered rabbit internal anal sphincter construct.

Bioengineered internal anal sphincter constructs stained positive for smooth muscle actin and βIII tubulin, confirming the presence of mature contractile smooth muscle and differentiated neurons, respectively. FIG. 6 depicts immunohistochemistry of rabbit bioengineered internal anal sphincter constructs. FIG. 6 at panel (A) shows a bioengineered rabbit internal anal sphincter construct stained positive for smooth muscle actin (scale bar 50 μm), indicating the maintenance of smooth muscle phenotype in the construct. FIG. 6 at panel (B) shows a bioengineered rabbit internal anal sphincter construct expressed positive βIII tubulin stain, indicating the presence of differentiated neurons in the construct (scale bar 20 μm).

Protein Expression using qPCR

Bioengineered internal anal sphincter constructs were obtained at days 7, 10, 11, 12, 13, and 14 post-fabrication. qPCR was performed to check for the presence of contractile smooth muscle cells and neural cells.

The objective was to test: (i) maturity of the smooth muscle cells in the bioengineered internal anal sphincter constructs using smooth muscle specific marker smoothelin and (ii) differentiation of the neural progenitor cells into mature neurons in the bioengineered internal anal sphincter constructs using βIII tubulin.

Figures 7A, 7B:
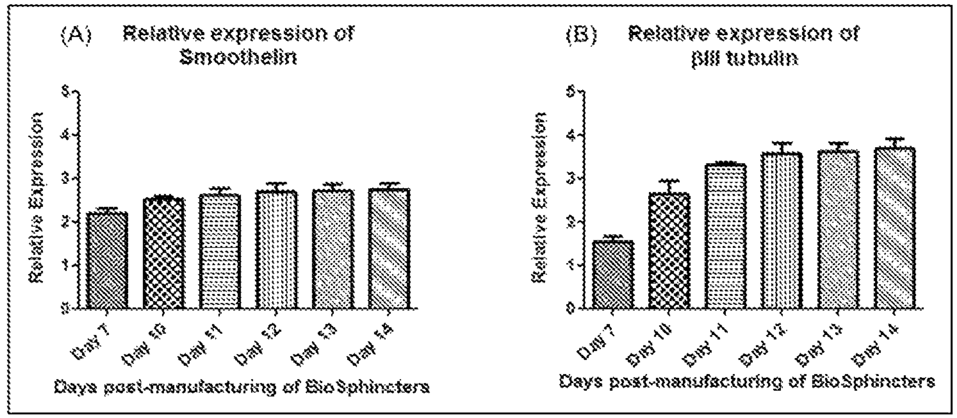
FIGS. 7A-7B provide exemplary data showing relative expression of Smoothelin and βIII tubulin.

Quantitative polymerase chain reaction (qPCR) was conducted to quantify genetic expression of smoothelin and βIII tubulin. Smoothelin in the bioengineered internal anal sphincter constructs was similar from day 7 to 10, 11, 12, 13 and 14 (without significant difference in the level of expression) indicating that maturity and contractile phenotype of smooth muscle was unaffected at those time points post-engineering. βIII tubulin expression increased significantly from day 7 to day 10 and reached plateau starting at day 12 through day 14, indicating that full differentiation of neural progenitor cells into neurons was reached by day 12 post-engineering. FIGS. 7A-7B provide exemplary data showing relative expression of Smoothelin and βIII tubulin. FIG. 7A depicts exemplary data showing that bioengineered internal anal sphincter constructs expressed smoothelin at a similar level starting at day 10, indicating that the smooth muscle component of these constructs reached maturity by day 10 and maintains it until through day 14. FIG. 7B depicts exemplary data showing that neural progenitor cells of bioengineered internal anal sphincter constructs start differentiating into mature neurons as early as day 7 post-fabrication. Neural differentiation reaches its maximum by day 12 with no significant difference in neural differentiation between days 11, 12, 13 and 14.

Physiological Testing of Constructs

Bioengineered internal anal sphincter constructs were tested for functionality using an isometric force transducer. Constructs were placed between a stationary central pin and the measuring arm of the organ bath transducer (Harvard Apparatus, Holliston MA). Bioengineered internal anal sphincter constructs were immersed in 4 mL of Dulbecco's Modified Eagle Medium buffered with 25 mM HEPES which was changed at the end of every experiment.

Figure 8:
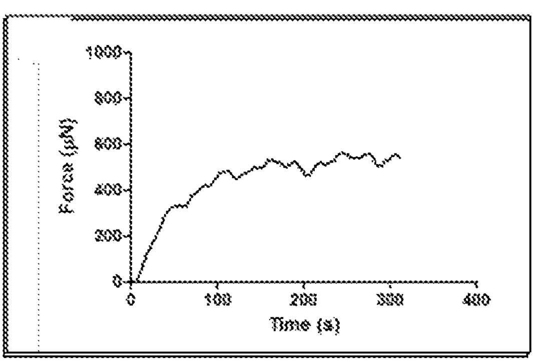
FIG. 8 is a graph of measured basal tone in bioengineered internal anal sphincter constructs.

Bioengineered internal anal sphincter constructs were maintained at 37° C. Bioengineered internal anal sphincter constructs established a spontaneous basal tone without any exogenous stimuli. That is, they were able to generate spontaneous basal tone in the absence of any external stimulation, a native characteristic of internal anal sphincters. FIG. 8 depicts exemplary basal tone data, that averaged 541±13 μN (n=10).

Generation of spontaneous basal tone is a characteristic of sphincter tissue. FIG. 9 depicts exemplary basal tone data quantified following pharmacological or electrical stimuli. Functionality of bioengineered internal anal sphincter constructs was established by baseline before any treatment.

Figures 9A, 9B:
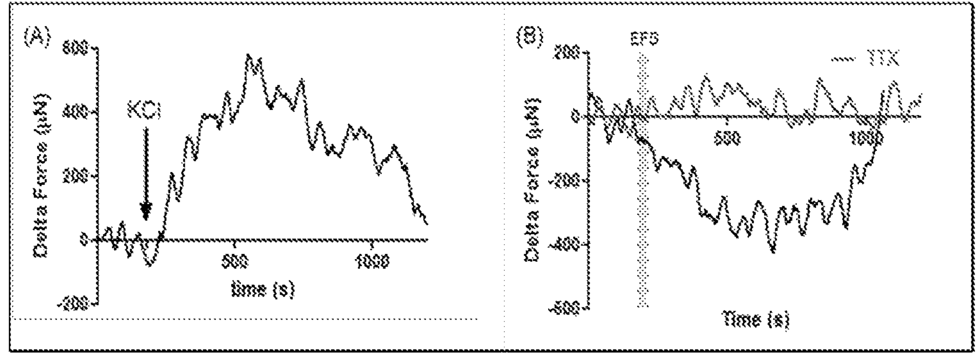
FIGS. 9A-9B provide further exemplary data of basal tone.

Muscle functionality was tested using addition of 60 mM potassium chloride (KCl). When bioengineered internal anal sphincter constructs established a baseline, addition of KCl caused a contraction above established basal tone, with maximal average contraction of 625±10 μN. FIG. 9A depicts exemplary data showing an addition of KCl. The addition induced smooth muscle depolarization followed by a robust contraction averaging 625±10 μN, indicating the functionality of the smooth muscle.

To test the neural functionality, neuronally evoked relaxation was achieved by electrical field stimulation (EFS) (5 Hz, 0.5 ms) between parallel platinum plate electrodes in the organ bath. FIG. 9B depicts exemplary data showing neural-mediated relaxation (−408±9 μN) of smooth muscle was achieved by EFS, which was abolished in the presence of TTX pre-treatment (red trace), indicating neural functionality in the bioengineered internal anal sphincter constructs. FIG. 9B also shows the maximal relaxation averaged −408±9 μN. EFS-mediated relaxation of the constructs was inhibited in the presence of neurotoxin tetrodotoxin (TTX), indicating that the relaxation was mediated by functional neurons in the bioengineered internal anal sphincter constructs.

Additional testing was performed on the bioengineered internal anal sphincter constructs to ensure functionality. Acetylcholine (Ach) caused a contraction of bioengineered Sphincter with an average of 363±8 μN, which was partially inhibited in the presence of neural blocker TTX (30-40% inhibition). This inhibition is attributed to the contribution of smooth muscle to the contraction as TTX blocks the response of the neural cells; consequently, the response recorded is interpreted as muscle-mediated. EFS-induced relaxation was also partially inhibited by nitric oxide neuron inhibitor (LNAME), indicating that the EFS-induced relaxation was partially mediated by functional nitric oxide neurons in the bioengineered internal anal sphincter constructs. Bioengineered internal anal sphincter constructs responded to both smooth muscle and neural pharmacological stimuli, indicating the functionality of both components. Results shown in this table are from 10 bioengineered internal anal sphincter constructs. Physiological data showed the consistency in functionality in the bioengineered internal anal sphincter constructs for implantation. A summary of data pertaining to the physiological functionality of bioengineered internal anal sphincter constructs, pre-implantation, is shown in below Table 3.

TABLE 3

Physiological Functionality of the Constructs

| | KCl | ACh | TTX-ACh | EFS | L-NAME- EFS | TTX-EFS |
|---|---|---|---|---|---|---|
| Mean ± SEM (μN) (n = 10) | 625 ± 10 | 363 ± 8 | 228 ± 7 | −408 ± 9 | −225 ± 6 | −168 ± 3 |

EXAMPLE 6

The present example discloses implanting fabricated constructs into the anorectum of rabbits. The present example also discloses characterization of implanted constructs.

Bioengineered internal anal sphincter constructs constructed using autologous cells isolated from biopsy were implanted approximately 6-8 weeks post biopsy procedure. Animals in the non-treated group did not go through any additional surgeries. During implantation surgery, general anesthesia was rendered using isoflurane via mask in animals in both the treated and sham surgery groups. Similar pre-operative procedures were performed as described for the biopsy procedure.

Figures 10A, 10B, 10C:
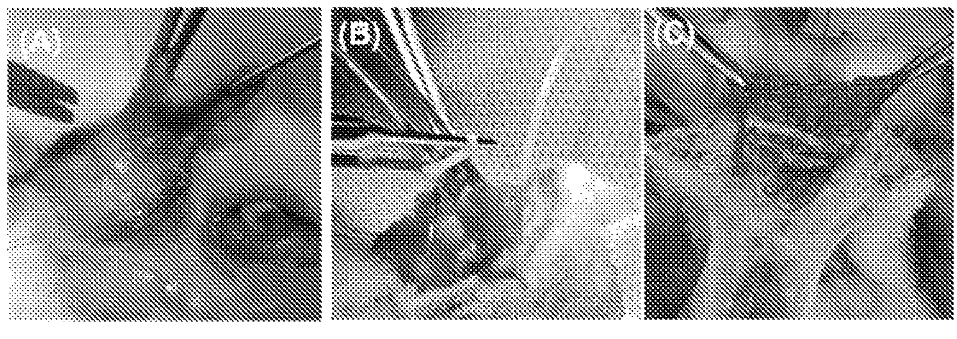
FIGS. 10A-10C depict implantation of the fabricated internal anal sphincter constructs.

The surgical site was appropriately prepared. A circumferential curvilinear incision through the anocutaneous tissue was made. FIG. 10 depicts implanting of the constructs. FIG. 10 at panel (A) depicts a circumferential incision was made around the anocutaneous junction of the anal canal.

The intersphincteric plane was identified and dissected for approximately 1 cm proximally. As space between the rabbit's own internal anal sphincter and external anal sphincter was created by dissecting a plane between the two anal sphincters. FIG. 10 at panel (B) depicts engineered autologous bioengineered internal anal sphincter constructs were placed in the intersphincteric space. FIG. 10 at panel (C) depicts engineered autologous bioengineered internal anal sphincter constructs were stacked circumferentially around the injury site as full muscle sphincters. FIG. 10 at panel (B) and FIG. 10 at panel (C), depict, in the treated group, 4 bioengineered internal anal sphincter constructs (day 12 post-engineering) were implanted in this created space. In the sham group, no bioengineered internal anal sphincter constructs were placed in the created space. Incisions were closed using simple-interrupted 5-0 prolene sutures.

In Vivo Efficacy Study

Anorectal manometry is a technique used to measure contractility in the anus and rectum. Anorectal manometry was performed initially at baseline prior to any surgery. These measurements reflected the control state for all animals in this study. Anorectal manometry was performed prior to any surgery (before animals went for any procedure) to record the baseline, and one month following internal anal sphincter hemi-sphincterectomy (biopsy), then at 3, 6, and 12 months in each experimental group. Light anesthesia was induced using isoflurane via mask. Following sedation, the rabbits were laid on their right side and the catheter was inserted into the rectum 6 cm deep. The catheter has four air-charged pressure transducers arranged at the same level circumferentially and 90° apart. The catheter was then withdrawn in 1 cm increments and the area of maximum resting pressure (anal basal pressure) was identified. Anal basal pressure was recorded. A balloon attached to the distal aspect of the catheter was used to evaluate RAIR, which is expressed as the percentage decrease in basal pressure in response to rectal balloon inflation to a volume of 20 mL. Data acquisition and analysis was performed using Bio-VIEW software (Sandhill Scientific, Littleton, CO, http://www.diversatekhealthcare.com/).

Statistical Analysis

One-way ANOVA was performed with Bonferroni post-hoc analysis to compare different groups at various time points. For rabbits in the non-treated group, anal basal pressure and RAIR readings at 1, 3, 6, and 12 months post-biopsy were significantly lower than those at baseline (prior to any surgery) with $p<0.0001$. In the treated group (rabbits that received implantation of 4 bioengineered internal anal sphincter constructs), anal basal pressure and RAIR readings at 1, 3, 6, and 12 months post-implantation were significantly higher than readings post-sphincterectomy and readings in the non-treated group at the respective time points, $p<0.0001$. In the sham surgery group, anal basal pressure and RAIR readings at 1, 3, 6, and 12 months post-sham surgery were significantly lower than those at baseline (prior to any surgery), $p<0.0001$ and not significantly different from rabbits in the non-treated group (only sphincterectomy) at the respective time points, $p>0.05$.

Figures 11A, 11B:
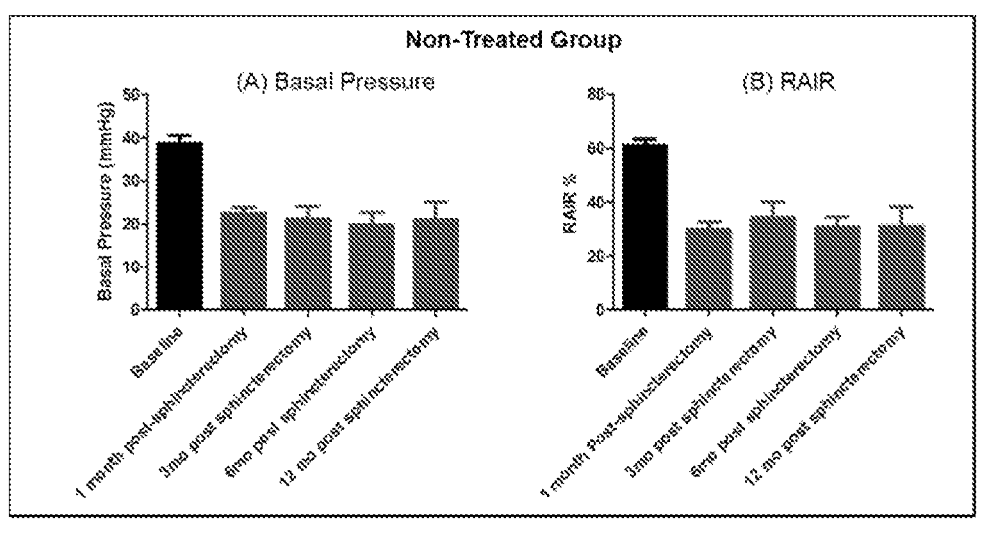
FIGS. 11A-11B provide exemplary data showing anal basal pressure and RAIR results for the non-treated group.

Basal Pressure:

FIG. 11A depicts exemplary data showing anal basal pressure in the non-treated group. Hemi-circumferential internal anal sphincterectomy resulted in significant decrease in basal tone in all groups at 1-month post-sphincterectomy. In the non-treated group, basal pressure remained low over the study period. Basal pressure decreased from 38.7±9 mmHg (n=26) to 22.5±1.3 mmHg at 1-month (n=26), 21.1±3.1 mmHg at 3 months (n=11), 19.8±2.9 mmHg at 6 months (n=10) and 21±4.2 mmHg at 12 months (n=5) post sphincterectomy ($p<0.0001$). Basal pressures at 1, 3, 6, and 12 months post-sphincterectomy were not significantly different from each other ($p>0.05$). Internal anal sphincter hemi-sphincterectomy induced a significant decrease in anal basal pressure from pre-sphincteric baseline to 1, 3, 6 and 12 months post-surgery. This indicated that the internal anal sphincter hemi-sphincterectomy induced sustained fecal incontinence in the rabbits in the non-treated group.

Figures 12A, 12B:
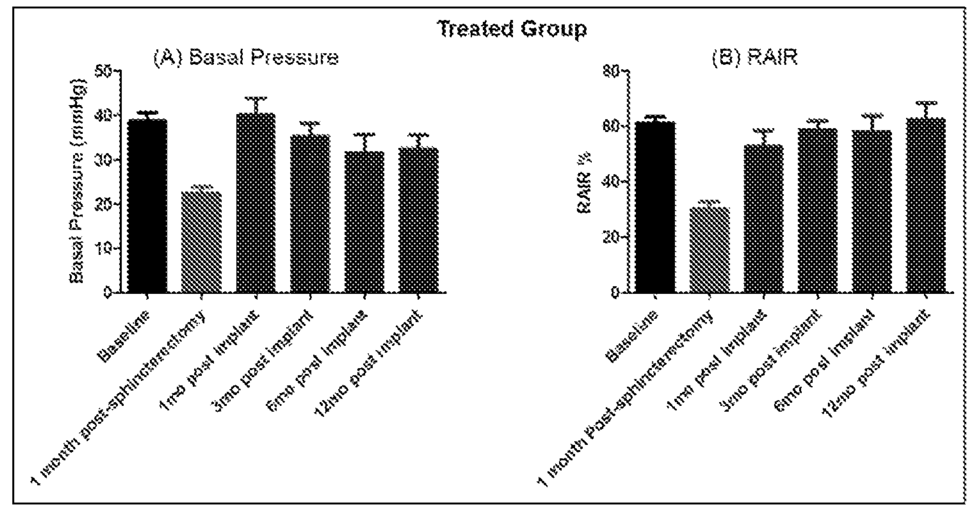
FIGS. 12A-12B provide exemplary data showing anal basal pressure and RAIR results for the treated group.

FIG. 12A depicts exemplary data showing anal basal pressure in the treated group. In the treated group prior to implantation, anorectal readings were performed on the rabbits following sphincterectomy to confirm their incontinence. Anorectal manometry readings following implantation of 4 bioengineered internal anal sphincter constructs were conducted on the rabbits (n=10) FIG. 12A. Basal pressure significantly increased following implantation of the bioengineered internal anal sphincter constructs (blue bars, $p<0.0001$) compared to basal pressure following sphincterectomy (22.5±1.3 mmHg). Anorectal manometry post-implantation indicated that basal pressure at 3 months (35.2±3 mmHg, n=10), 6 months (37.0±3.4 mmHg, n=7), and 12 months (32.4±3.1 mmHg, n=7) was restored back to normal compared to baseline ($p>0.05$). Internal anal sphincter hemi-sphincterectomy induced significant decrease in anal basal pressure (red bars) compared to pre-sphincteric baseline (black bar). Following implantation of the bioengineered internal anal sphincter constructs, anal basal pressure was restored to normal values when followed up to 12 months.

Figures 13A, 13B:
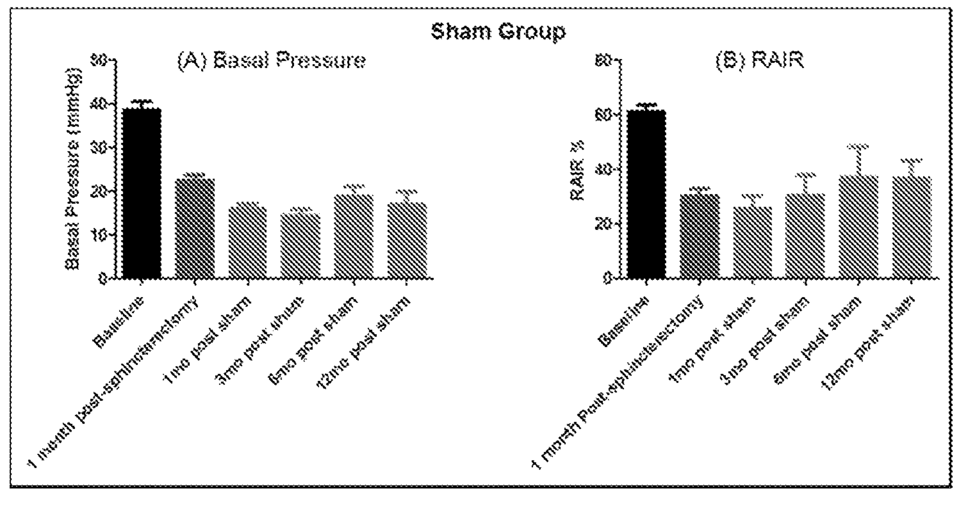
FIGS. 13A-13B provide exemplary data showing anal basal pressure and RAIR results for the sham group.

FIG. 13A depicts exemplary data showing anal basal pressure in the sham group. In the sham surgery group, basal pressure was significantly reduced from 38.7±9 mmHg (baseline) to 16±1.1 mmHg at 1-month time point, 14.5±1.5 mmHg at 3-month time point, 18.8±2.3 mmHg at 6-month time point, and 16.9±2.9 mmHg at 12-month time point post-sham (n=5, $p<0.0001$) FIG. 13 at panel (A). Basal pressure at 1, 3, 6, and 12 months post sham was not significantly different from basal pressure at 1, 3, 6, and 12 months post-sphincterectomy (non-treated group) ($p>0.05$), however it was significantly lower than basal pressure post-implantation at 1, 3, 6, and 12 months ($p<0.05$). Internal anal sphincter hemi-sphincterectomy induced significant decrease in anal basal pressure (red bars) compared to pre-sphincteric baseline (black bar). Following sham surgery, anal basal pressure remained significantly lower than baseline for up to 12 months post-sham surgery, but similar to post-sphincterectomy (red bar). This indicates that implantation of the bioengineered internal anal sphincter constructs was effective at restoring normal basal pressures.

Rectoanal Inhibitory Reflex RAIR:

FIG. 11B depicts exemplary data showing RAIR in the non-treated group. Sphincterectomy induced a significant decrease in RAIR in all rabbits. In the non-treated group, RAIR significantly decreased from 61.1±2.4% (baseline, n=26) to 30±2.7% at 1 month (n=26), 34.2±5.9% at 3 months (n=11), 30.6±3.8% at 6 months (n=10) and 31±7.3% at 12 months (n=5) post-sphincterectomy ($p<0.0001$) FIG. 11 at panel (B). RAIR at 1, 3, 6, and 12 months post-sphincterectomy were not significantly different from each other ($p>0.05$). Internal anal sphincter hemi-sphincterectomy induced a significant decrease in RAIR from pre-sphincteric baseline to 1, 3, 6 and 12 months post-surgery.

This indicated that the internal anal sphincter hemi-sphincterectomy induced sustained fecal incontinence in the rabbits in the non-treated group.

FIG. 12B depicts exemplary data showing RAIR in the treated group. In the treated group, following implantation of 4 bioengineered internal anal sphincter constructs, RAIR was restored to baseline and was found to be significantly higher (blue bars) than RAIR post-sphincterectomy in the non-treated group ($p<0.0001$) FIG. 12 at panel (B). RAIR in the treated group increased to 52.7±5.8 at 1 month, 58.6±3.3% at 3 months (n=10), 60.5±5.7% at 6 months (n=7), and 62.5±5.9% at 12 months (n=7). Internal anal sphincter hemi-sphincterectomy induced significant decrease in RAIR (red bars) compared to pre-sphincteric baseline (black bar). Following implantation of the bioengineered internal anal sphincter constructs, RAIR was restored to normal values when followed up to 12 months.

FIG. 13B depicts exemplary data showing RAIR in the sham group. In the sham surgery group, RAIR was also significantly reduced from 61.1±2.4% (baseline) to 25.6±4.6% at 1-month post-sham (n=5), 30.5±7.3% at 3-month time point (n=5), 37.2±11.2% at 6-month time point (n=5), and 36.6±6.6% at 12-month time point (n=5) FIG. 13 at panel (B). RAIR at 1, 3, 6, and 12-months post sham was not significantly different from RAIR at 1, 3, 6, and 12 months post-sphincterectomy (non-treated group) ($p>0.05$); however, it was significantly lower than RAIR at 1, 3, 6, and 12 months post-implantation ($p<0.05$). Internal anal sphincter hemi-sphincterectomy induced significant decrease in RAIR (red bars) compared to pre-sphincteric baseline (black bar). Following sham surgery, RAIR remained significantly lower than baseline for up to 12 months post-sham surgery, but similar to post-sphincterectomy (red bar). This indicates that implantation of the bioengineered internal anal sphincter constructs was effective at restoring normal RAIR.

Table 4 and Table 5 below summarize the Basal Pressure and RAIR in the three Experimental Groups. FIG. depicts exemplary data summarize the Basal Pressure and RAIR in the three Experimental Groups.

TABLE 4

| Anorectal Manometry Readings (Basal Pressure). | | | | | | |
|---|---|---|---|---|---|---|
| | | | 1 month post sphincterectomy | 3 months post sphincterectomy | 6 months post sphincterectomy | 12 months post sphincterectomy |
| Baseline n = 26 | 1 month post sphincterectomy n = 26 | Non-treated group | 22.5 ± 1.3 | 21.1 ± 3.1 | 19.8 ± 2.9 | 21 ± 3.2 |
| | | | 1 month post implant | 3 months post implant | 6 months post implant | 12 months post implant |
| 38.7 ± 1.9 | 22.5 ± 1.3 | Treated group | 40.1 ± 3.8 | 35.2 ± 3.0 | 34.6 ± 4.1 | 32.4 ± 3.1 |
| | | | 1 month post sham | 3 months post sham | 6 months post sham | 12 months post sham |
| | | Sham surgery group | 16 ± 1.1 | 14.5 ± 1.5 | 18.8 ± 2.3 | 16.9 ± 2.9 |

Basal Pressure (mmHg) (mean ± SEM)

TABLE 5

| Anorectal Manometry Readings (RAIR). | | | | | | |
|---|---|---|---|---|---|---|
| | | | 1 month post sphincterectomy | 3 months post sphincterectomy | 6 months post sphincterectomy | 12 months post sphincterectomy |
| Baseline n = 26 | 1 month post sphincterectomy n = 26 | Non-treated group | 30 ± 2.7 | 34.2 ± 5.9 | 30.6 ± 3.8 | 31 ± 5.6 |
| | | | 1 month post implant | 3 months post implant | 6 months post implant | 12 months post implant |
| 61.1 ± 2.4 | 30 ± 2.7 | Treated group | 52.7 ± 5.8 | 58.6 ± 3.3 | 60.2 ± 5.7 | 62.5 ± 5.9 |
| | | | 1 month post sham | 3 months post sham | 6 months post sham | 12 months post sham |
| | | Sham surgery group | 25.6 ± 4.6 | 30.5 ± 7.3 | 37.2 ± 11.2 | 36.6 ± 6.6 |

RAIR (%) (mean ± SEM)

Optimization of a Number of Constructs to be Implanted to Restore Functionality

A separate study was carried out to optimize the dosage. The study included three groups of rabbits: group 1 with three rabbits had implantation of 2 bioengineered internal anal sphincter constructs, group 2 with 10 rabbits had implantation of 4 bioengineered internal anal sphincter constructs, and group 3 with 2 rabbits had implantation of 6 bioengineered internal anal sphincter constructs. Rabbits were followed regularly by anorectal manometry for anal basal pressure and RAIR. Manometry readings were compared among rabbits that received 2, 4, and 6 bioengineered internal anal sphincter constructs at the 3-month time point.

Figure 14A:
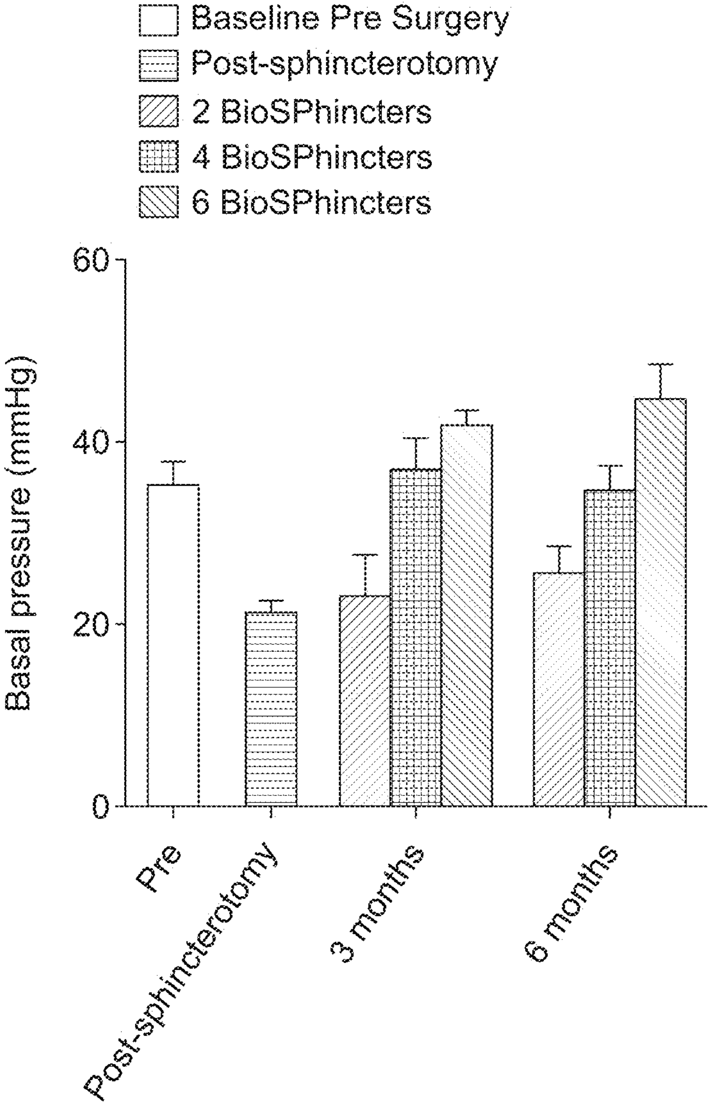
FIGS. 14A-14B provide exemplary data showing anorectal manometry comparing rabbits receiving different doses of implanted bioengineered internal anal sphincter constructs, 2, 4, or 6 bioengineered internal anal sphincter constructs.
Figure 14B:
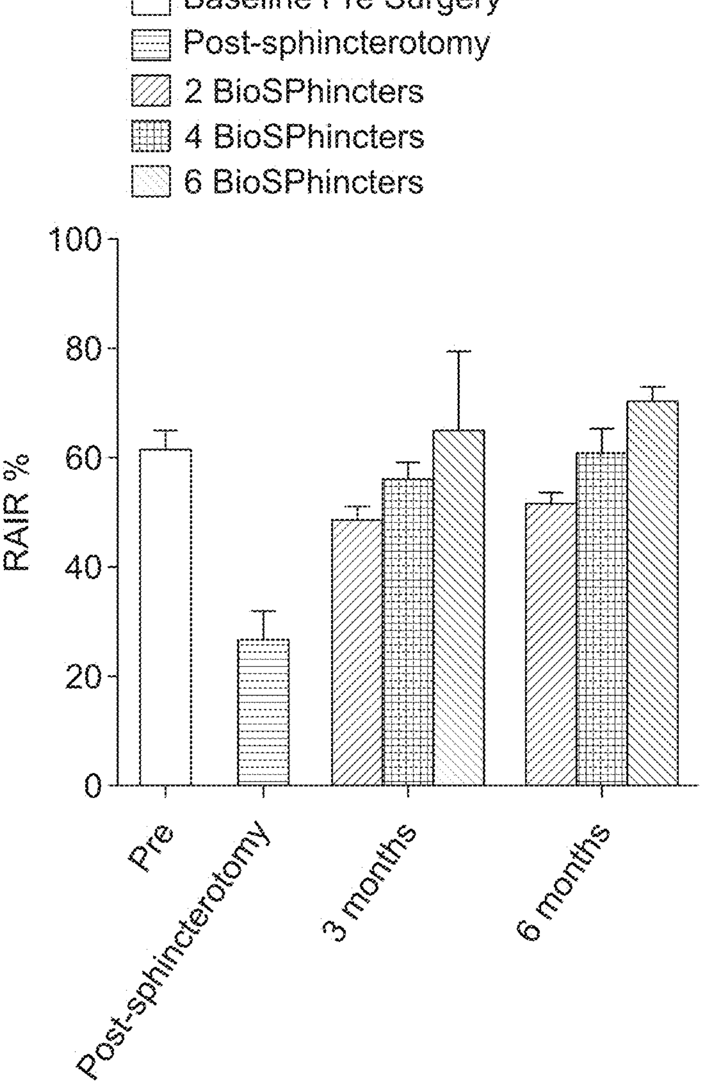

FIG. 14 depicts exemplary data showing the dose of implanted bioengineered internal anal sphincter constructs. Anorectal manometry was performed regularly on the rabbits that received 2, 4, or 6 Bioengineered Sphincters Bars express the mean of standard error of independent samples per group, ($p<0.05$).

Basal Pressure:

FIG. 14 at panel (A) depicts exemplary data showing anorectal manometry post-implantation indicated that basal pressure at 3 months was increased to 23.0±4.4 mmHg, 35.2±3 mmHg, and 42±1.5 mmHg after implantation of 2 bioengineered internal anal sphincter constructs (n=3), 4 bioengineered internal anal sphincter constructs (n=10), and 6 bioengineered internal anal sphincter constructs (n=2), respectively. Basal pressures at three months following implantation of 2, 4, or 6 bioengineered internal anal sphincter constructs were significantly different from each other. This trend remained similar after six months as well. The basal pressure following six months implantation was increased to 25.53±3.0 mmHg for 2 bioengineered internal anal sphincter constructs, 37.0±3.4 mmHg for 4 bioengineered internal anal sphincter constructs, and 44.8±3.5 mmHg for 6 bioengineered internal anal sphincter constructs.

RAIR (Recto-Anal Inhibitory Reflex) Measurement

FIG. 14 at panel (B) depicts exemplary data showing RAIR was recorded for the rabbits implanted with different numbers of bioengineered internal anal sphincter constructs. After three months of implantation, RAIR was increased to 48.7±2.4% following implantation of 2 bioengineered internal anal sphincter constructs (n=3), 58.6±3.3% following implantation of 4 bioengineered internal anal sphincter constructs (n=10), and 64.9±14.6% following implantation of 6 bioengineered internal anal sphincter constructs (n=2). RAIR at three months following implantation of 2, 4, or 6 bioengineered internal anal sphincter constructs were different from each other ($p<0.05$). After six months of implantation RAIR improved in a similar trend: with implantation of 2 bioengineered internal anal sphincter constructs resulting in 51.6±2.0%, 4 bioengineered internal anal sphincter constructs resulting in 60.5±5.7%, and 6 bioengineered internal anal sphincter constructs resulting in 70.15±2.5% of RAIR, which were significantly different from each other ($p<0.05$).

Following implantation of 2 bioengineered internal anal sphincter constructs, basal pressure and RAIR were not significantly improved from that measured post-sphincterectomy. The results indicated that implantation of both 4 and 6 bioengineered internal anal sphincter constructs were able to significantly improve the basal pressure and RAIR back to pre-sphincterectomy levels within 3 months; however, the restoration trend differed between the 4 and 6 bioengineered internal anal sphincter constructs conditions after 6 months. Although the basal pressure after 6 months of implantation of 6 bioengineered internal anal sphincter constructs was significantly higher than that of 4 bioengineered internal anal sphincter constructs at 6 months and pre-sphincterectomy measurements, fecal output for rabbits implanted with 6 bioengineered internal anal sphincter constructs was altered in that fecal pellets became lodged in the rectum and required manual evacuation. Implantation of 4 bioengineered internal anal sphincter constructs however, restored basal anorectal pressure (37.0±3.4) and RAIR (60.5±5.7) values to baseline basal pressure (38.7±1.9) and RAIR (61.1±2.4) of respective animals. It was therefore concluded that 4 bioengineered internal anal sphincter constructs is an optimal dose for treating fecal incontinence and restoring the basal pressure.

Improvement in Fecal Hygiene:

The internal anal sphincter hemi-sphincterectomy affected fecal hygiene of the rabbits. This was evident from messy rabbit cages as feces were dispersed over the whole area of the cage. There was definite lack of anal area hygiene as the area was always covered in a thin layer of feces. After implantation, the fecal hygiene returned to normal with a clean anal area and normal defecatory movement.

Interpretation of Manometry Data:

Internal anal sphincter hemi-sphincterectomy resulted in a significant decrease in anal basal pressure and RAIR compared to baseline (no surgery), supporting the validity of the induced-incontinence model.

Implantation of 4 bioengineered internal anal sphincter constructs following a hemi-sphincterectomy restored both anal basal pressure and RAIR to levels significantly higher than values observed in the non-treated group.

In the sham surgery group, anal basal pressure and RAIR were not improved and were comparable to readings from rabbits in the non-treated group, indicating that the scarring and fibrosis due to the second surgery did not restore basal tone or RAIR.

Compared to non-treated and sham surgery groups, manometry readings in the treated group confirmed that the bioengineered internal anal sphincter constructs were viable and functional in vivo with maintenance of both the muscle and neural components.

Implantation of 2 bioengineered internal anal sphincter constructs was insufficient to restore the basal pressure and RAIR to normal levels. The implantation of 6 bioengineered internal anal sphincter constructs resulted in an excessive increase in both basal pressure and RAIR, which is undesirable for healthy anorectal physiology. Implantation of 4 bioengineered internal anal sphincter constructs appeared optimal for restoring basal anal pressure and RAIR measurements to levels observed with normal animals.

Histopathology Endpoints

Tissues were collected at necropsy. They were removed, fixed in 4% neutral buffered formalin or paraformaldehyde, transferred to 70% alcohol, embedded in paraffin, and sectioned. The sections were stained with Hematoxylin and Eosin (H&E) and Masson's trichrome.

Figures 15A, 15B:
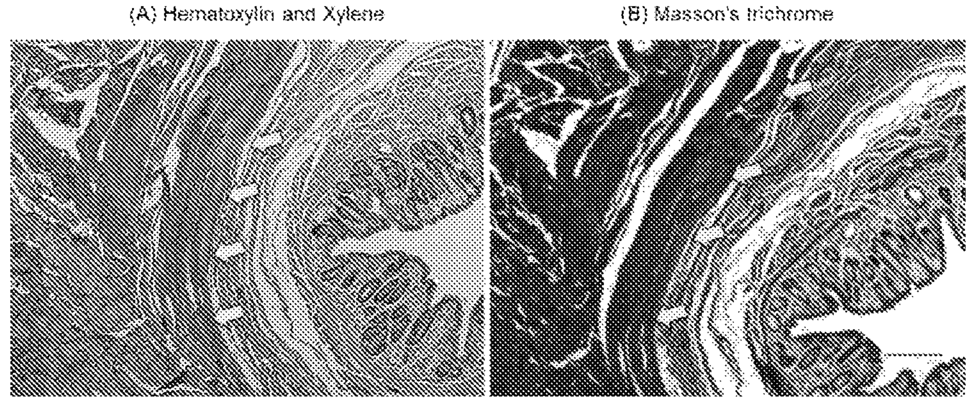
FIGS. 15A-15B provide histological analyses of the anal site.

The collected tissues displayed an intact bioengineered internal anal sphincter construct after 12 months of implantation. FIG. 15 depicts a histological analysis of the anal site following implantation. FIG. 15 at panel (A) depicts H&E stained sections of the implanted site confirmed the appearance of bioengineered internal anal sphincter constructs. H&E staining displayed presence of thick continues band of implanted IAS integrated with extra-cellular matrix. The thick continuous sheet of internal anal sphincter tissues validated the manometry outcomes. There was absence of any fibrosis or avascular collagen around the implant, indicating no foreign-body reaction with the implants. FIG. 15 at panel (B) depicts sections stained with Masson's trichrome. Masson's trichrome staining confirmed muscle sheet as red coloration with collagen deposition represented in blue coloration. The implanted constructs showed abundant red stained smooth muscle cells interspersed with the blue stained collagen. Scale bar 500 μm Migration and Distribution of Cells from Implant:

The migration study for implanted cells was carried out in two different study groups. In one set of the study, rabbits (n=3) received the bioengineered internal anal sphincter constructs with transduced smooth muscle cells with stable lentiviral green fluorescent protein (GFP) particles. In the other study group, the neural progenitor cells of bioengineered internal anal sphincter constructs were transduced with stable lentiviral green fluorescent protein (GFP) particles and implanted in rabbits (n=3). After 6 months of implantation, the bioengineered internal anal sphincter constructs were harvested and cell migration and distribution of implanted cells was analyzed. In both groups, the implantation site was sectioned in transverse plane. The implant stability, cell distribution, and migration were studied via immunohistochemical analysis.

Figures 16A, 16B, 16C, 16D:
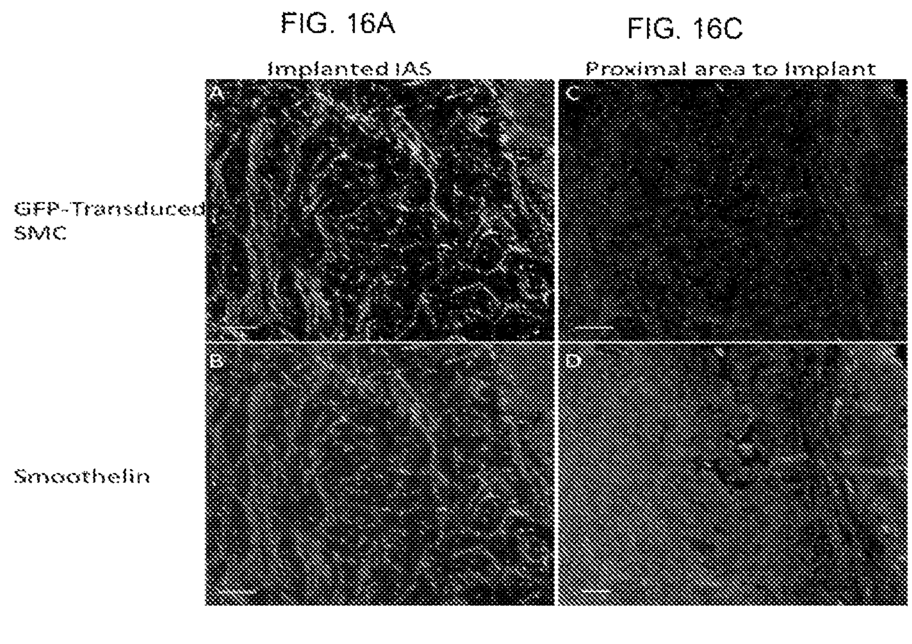
FIGS. 16A-16D depicts post-implant immunohistochemical analysis of bioengineered internal anal sphincter constructs generated with transduced smooth muscle cells.

Bioengineered Internal Anal Sphincter Constructs with Transduced Smooth Muscle Cells:

FIG. 16 depicts post-implant immunohistochemical analysis of bioengineered internal anal sphincter constructs generated with transduced smooth muscle cells. The implanted bioengineered internal anal sphincter constructs with green fluorescent protein-transduced smooth muscle cells and adjacent tissue was harvested, sectioned in the transverse direction, and stained with the functional muscle marker smoothelin. FIG. 16 at panel (A) depicts transverse sections of implanted internal anal sphincters displayed well distributed, circular oriented (upwards to downwards), green fluorescent protein transduced smooth muscle cells (green) integrated with adjacent tissues. FIG. 16 at panel (B) depicts implanted smooth muscle cells confirmed with immunoreactivity with smoothelin (red). FIG. 16 at panel (C) depicts the proximal area of the implanted internal anal sphincter displayed absence of any green fluorescent protein-transduced smooth muscle cells, there was no cell migration. In this transverse section, the implanted cells were uniformly distributed and oriented in a circular direction around the anus. The implanted cells integrated with native tissue but did not migrate from the implantation site into the proximal areas. FIG. 16 at panel (D) depicts the proximal area to the implant was positive to smoothelin. The bioengineered internal anal sphincter constructs and adjacent tissues displayed positive immunoreactivity towards smoothelin, indicating functional muscle cells. All the images are counterstained with DAPI nuclear stain (scale bar 100 μm).

Figures 17A, 17B, 17C, 17D, 17E, 17F:
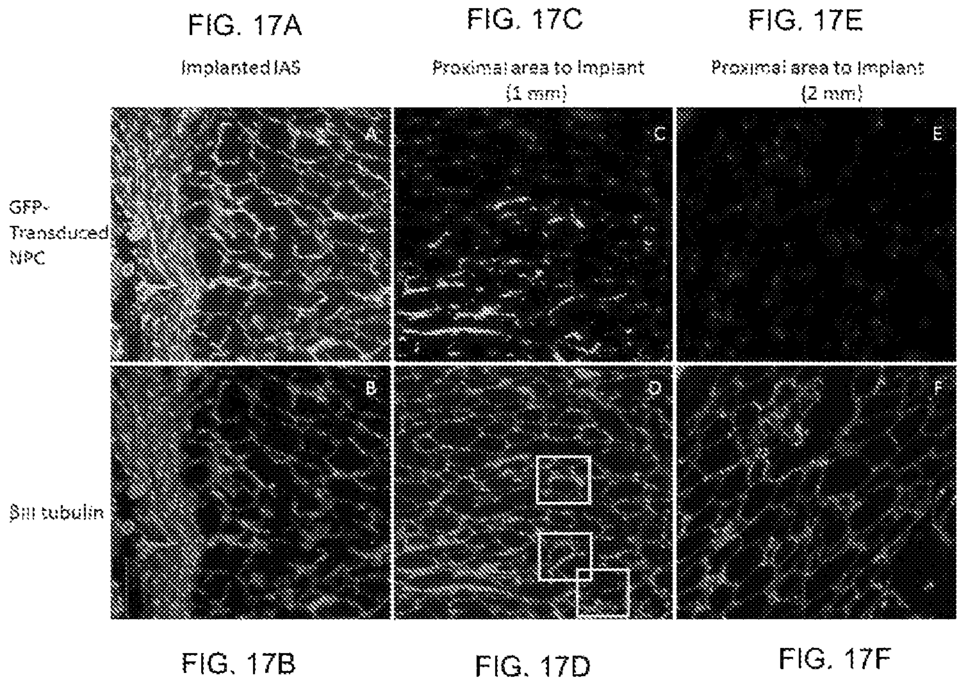
FIGS. 17A-17F provide immuno-histochemical analysis of bioengineered internal anal sphincter constructs post-implant generated with transduced neural progenitor cells.

Bioengineered Internal Anal Sphincter Constructs with Transduced Neural Progenitor Cells:

FIG. 17 depicts post-implant immunohistochemical analysis of bioengineered internal anal sphincter constructs generated with transduced neural progenitor cells. The implanted bioengineered internal anal sphincter constructs with green fluorescent protein-transduced neural progenitor cells and adjacent tissue was harvested and stained with the functional neuronal marker βIII-tubulin. The bioengineered internal anal sphincter constructs and adjacent tissues displayed positive immunoreactivity towards βIII-tubulin, indicating differentiation of neural progenitor cells towards functional neurons.

FIG. 17 at panel (A) depicts transverse sections of internal anal sphincter displayed innervation and connectivity of transduced neural progenitor cells (green). FIG. 17 at panel (B) Immunoreactivity with βIII tubulin confirmed the differentiation of implanted neural progenitor cells (red). In the proximal region, FIG. 17 at panel (C) the transduced neural progenitor cells migrated up to 1 mm, where all green fluorescent protein transduced neurons (green). FIG. 17 at panel (D) depicts transverse sections of internal anal sphincter expressing βIII tubulin (red). The transduced neurons connected with native neurons up to 1 mm to 2 mm, where transduced neurons and native neurons displayed combined immunoreactivity to βIII tubulin and exhibited integration, synaptic junctions with native neurons (as displayed in the yellow box). FIG. 17 at panel (E) depicts an absence of green neurons in 2 mm region confirmed that there was no migration of implanted neurons beyond 2 mm. FIG. 17 at panel (F) depicts where native neuron displayed βIII tubulin expressions. All the images counterstained with DAPI nuclear stain. (scale bar—200 μm).

Adjacent areas of implanted bioengineered internal anal sphincter constructs were analyzed for innervation and migration. The neurons of implanted bioengineered internal anal sphincter constructs were fluorescent in green color (green fluorescent protein transduction) and functional neurons were distinguished in red coloration owing to immunoreactivity with βIII-tubulin. These images confirmed integration and synaptic junctions of implanted cells with native neurons (as displayed in the yellow boxes; see FIG. 17 at panel (D). The implanted neural progenitor cells displayed innervation and connectivity up to ~2 mm. There was no migration of the implanted neurons beyond 2 mm.

Improvement in defecatory activity were observed as early as 3 weeks after implantation of the bioengineered internal anal sphincter constructs. Stool consistency returned to a firm pellet, similar to what was observed before fecal incontinence was induced by the sphincterectomy.

Similar studies to those described above for the rabbits the following examples disclose studies that were done on human cells in GMP facilities.

EXAMPLE 7

The present example discloses methods of biopsying human tissue for smooth muscle cells and neural progenitor cells.

Collecting a Small Intestine Biopsy and Internal Anal Sphincter Biopsy

Two biopsies will be collected from the same patient. The first, a biopsy from the small intestinal tissue (≥200 mg) will be obtained laparoscopically and will be used to provide autologous neural progenitor cells for the patient's bioengineered Sphincter construct. The second, a biopsy from the internal anal sphincter (≥200 mg) will be obtained through surgical retrieval and will provide autologous smooth muscle cells for the patient's bioengineered Sphincter construct.

EXAMPLE 8

The present example discloses isolating smooth muscle cells and neural progenitor cells from human biopsy samples.

Isolating—Dissection and Enzymatic Digestion

Neural Progenitor Cells:

The small intestine biopsy will be taken out of the transport solution container and washed with antibiotic solution (HBSS with 240 μg/ml Gentamicin, 160 μg/ml Vancomycin, 500 μg/ml Ceftazidime, 5.4 μg/ml Amphotericin B and 200 μg/ml Amikacin) three times with shaking (100 rpm) for at least 10 min each wash. The biopsy tissue will be weighed in order to determine the required volume of digestion solution, then washed three times in disinfection solution (HBSS with 5 μg/ml Gentamicin) for 2 min each wash at room temperature.

The tissue will then be placed on a sterile dish and cleaned of any fat or blood vessels with sterile scissors or scalpel. Using a sterile blade, the biopsy tissue is minced into fine pieces then washed three times in disinfection solution at room temperature using centrifugation at 600 μg for 5 min each wash. Following the last wash, the minced tissue will be incubated with digestion solution (18.5 μl/ml collagenase HA and 26.1 μl/ml BP protease) for 1 hour with shaking (100 rpm) at 37° C.

The digested tissue will be centrifuged at 400×g for 5 minutes, after which the supernatant will be passed through a 70 μm cell strainer into a new sterile conical tube (appropriately labeled) and stored at 2-8° C. The remaining pellet will be subjected to a second enzymatic digest (18.5 μl/ml collagenase HA and 26.1 μl/ml BP protease) for approximately 45 minutes with shaking (100 rpm) at 37° C.

Following the second digest, the remaining tissue will be centrifuged at 400×g for 5 minutes and the supernatant passed through a 70 μm cell strainer into a new sterile conical tube (appropriately labeled). Both tubes that contain the 70 μm suspension will be combined into one conical tube. The cells in the combined suspension are pelleted and washed at least three times by resuspending them in disinfection solution followed by centrifugation for 10 min at 2000×g; 15° C. A portion of the last wash will be collected for sterility testing.

The cell pellet is then resuspended in warm neural growth media by gentle pipetting. The dissociated pellet is passed through a 40 μm cell strainer into a new conical tube to select neural progenitor cells based on size. The filtered cells are plated into non-tissue culture treated vessels and cultured for approximately 4 weeks in a humidified incubator at 37° C. with 7% $CO_2$. Growth will be monitored approximately every other day by phase contrast microscopy and the cultures supplemented once a week with neural progenitor cell growth media.

Smooth Muscle Cells:

The internal anal sphincter biopsy will be taken out of the transport solution tube and washed in antibiotic solution (HBSS with 240 μg/ml Gentamicin, 160 μg/ml Vancomycin, 500 μg/ml Ceftazidime, 5.4 μg/ml Amphotericin B and 200 μg/ml Amikacin) three times with shaking (100 rpm) for at least 10 minutes each wash. The biopsy tissue will be weighed to determine the required volume of digestion solution to be made, then washed four times in disinfection solution (HBSS with 5 μg/ml Gentamicin) at room temperature for 2 minutes each wash. The tissue will be cleaned of any fat or blood vessels with sterile scissors or scalpel on a sterile dish, then minced into fine pieces using a sterile blade. The minced tissue is transferred into a sterile conical tube and washed three times with disinfection solution by centrifugation at 600×g for 5 minutes each wash, then incubated with digest solution (1 mg/ml collagenase DE) for 1 hour, with shaking (100 rpm) at 37° C. The digested tissue is centrifuged at 600×g for 5 minutes then washed three times using disinfection solution and centrifugation at 600×g for 5 minutes each wash. Following the third wash, the pellet is subjected to a second enzymatic digest (1 mg/ml collagenase DE) for approximately 45 minutes, with shaking at 100 rpm at 37° C. Following the second digest, remaining tissue is centrifuged at 600×g for 5 minutes, followed by at least three centrifugation washes with disinfection solution; 5 minutes each at 600×g. A portion of the last wash will be collected for sterility testing. The pellet is then resuspended by gentle pipetting in fresh smooth muscle growth media warmed to 37° C. The dissociated cells are plated into tissue culture vessels and incubated in a humidified incubator at 37° C. with 5% $CO_2$ for 4-5 days to facilitate cell attachment. After 4-5 days, fresh media will be supplemented to all vessels every other day regularly.

EXAMPLE 9

The present example discloses characterization of isolated human smooth muscle cells and isolated human neural progenitor cells from biopsy samples.

Smooth Muscle Cells

Figures 18A, 18B:
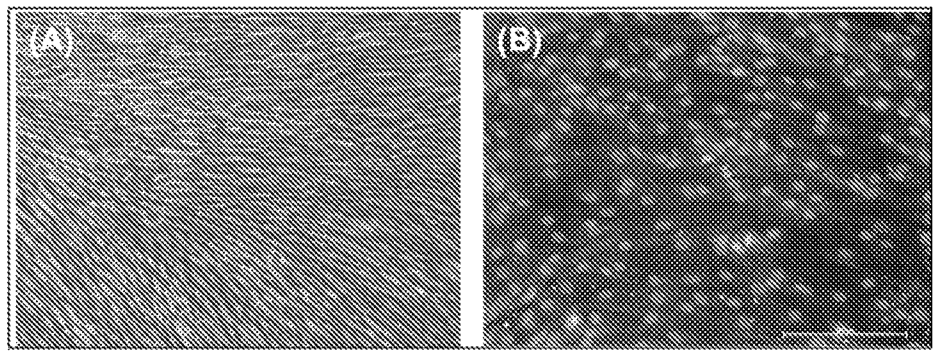
FIGS. 18A-18B provide microscopic characterization of isolated human smooth muscle cells.

Smooth muscle cells were isolated from the internal anal sphincter biopsy acquired a spindle-like morphology, normal morphology of smooth muscle as demonstrated in by microscopic evaluation are shown in FIG. 18 at panel (A). Additionally, cells stained positively for smooth muscle cell specific, smoothelin, by immunohistochemistry are shown in FIG. 18 at panel (B).

Figure 19A:
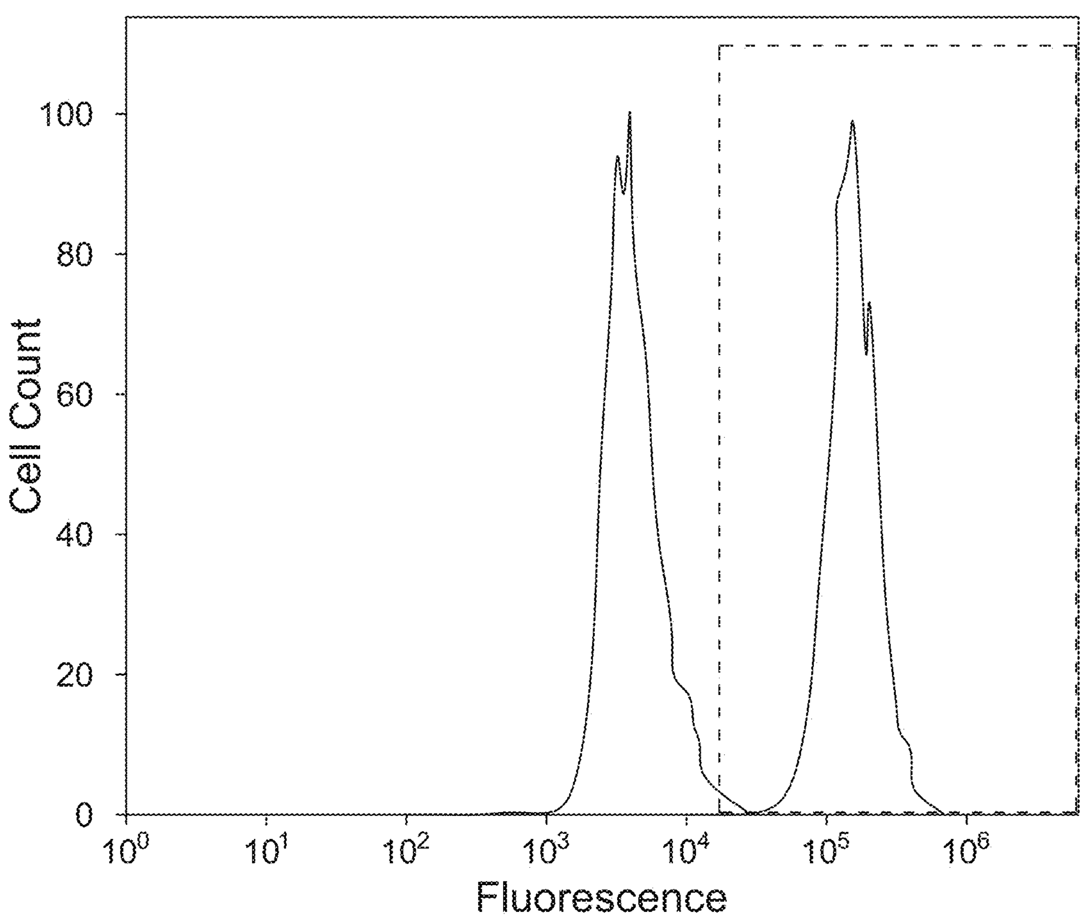
FIGS. 19A-19B provide exemplary flow cytometry analyses of isolated human internal anal sphincter smooth muscle cells.
Figure 19B:
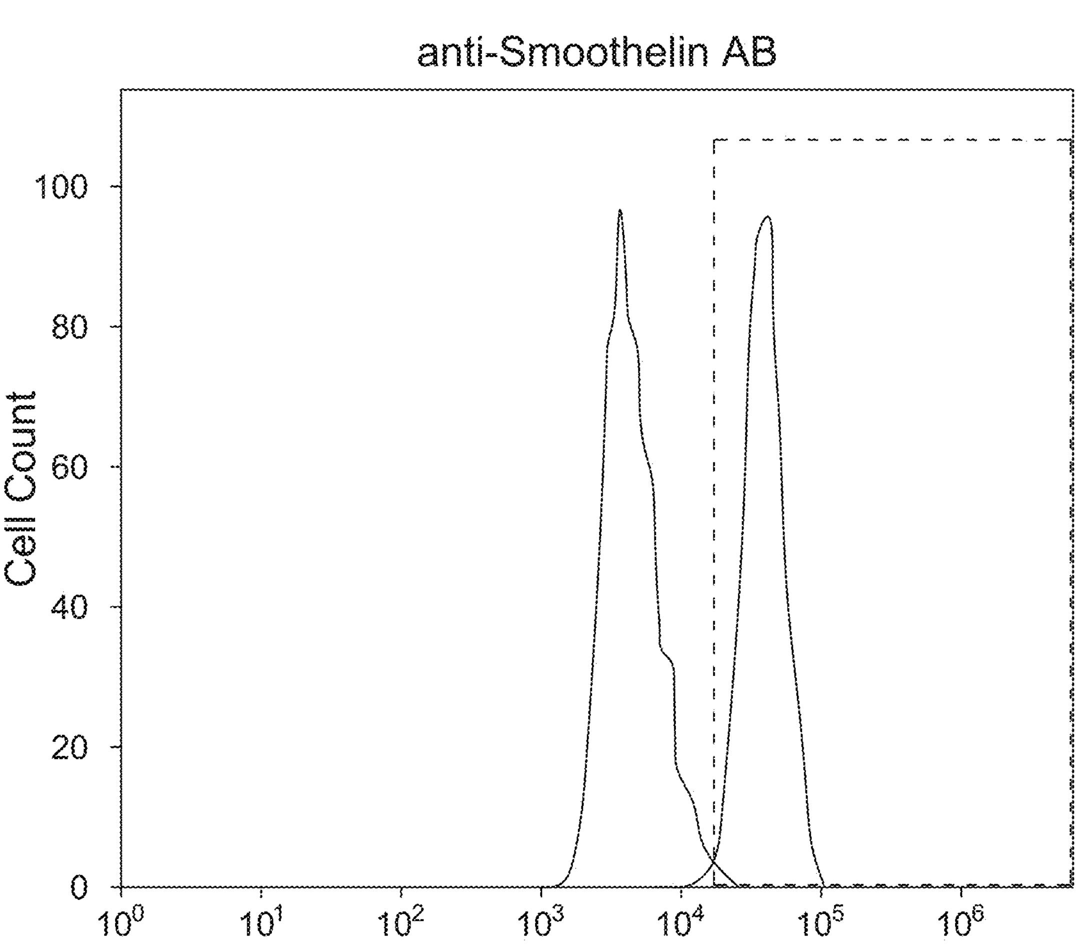

Flow cytometry was performed to characterize the phenotype of isolated, cultured human smooth muscle cells. Smooth muscle cells were incubated with anti-α-smooth muscle actin and anti-smoothelin primary antibodies followed by the appropriate fluorescent secondary antibodies. Cells incubated with fluorescent secondary antibody only were used as controls. Flow cytometry analysis demonstrated a high percentage of smooth muscle cells expressing both muscle specific antigens; α-smooth muscle actin and smoothelin, indicating the purity of the culture. As depicted in FIG. 19 at panel (A), analysis of flow cytometry results showed ~99.1% (98.4%-99.8%, n=3) of cells expressed smooth muscle actin. As depicted in FIG. 19 at panel (B), analysis of flow cytometry results showed ~95.4% (92.3%-98.7%, n=3) expressed smoothelin.

Figure 20:
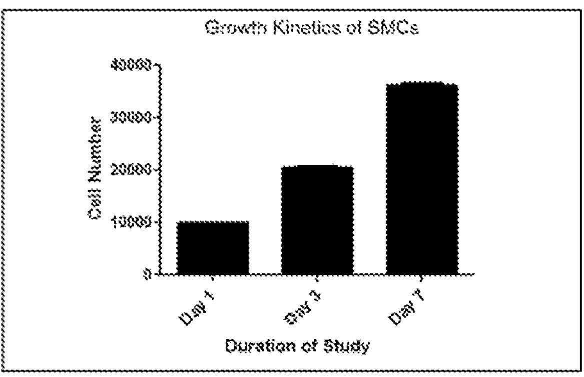
FIG. 20 depicts exemplary growth kinetics data of human smooth muscle cells.

Growth kinetics were determined by culturing isolated human smooth muscle cells for 7 days and measuring proliferation by cell counting. Cells were seeded in triplicate into six well plates at a density of 10,000 cells/well and followed over seven days. FIG. 20 shows cell numbers at 1, 3 and 7 days. The rate of cell proliferation was similar throughout the study.

Neural Progenitor Cells

Figures 21A, 21B, 21C:
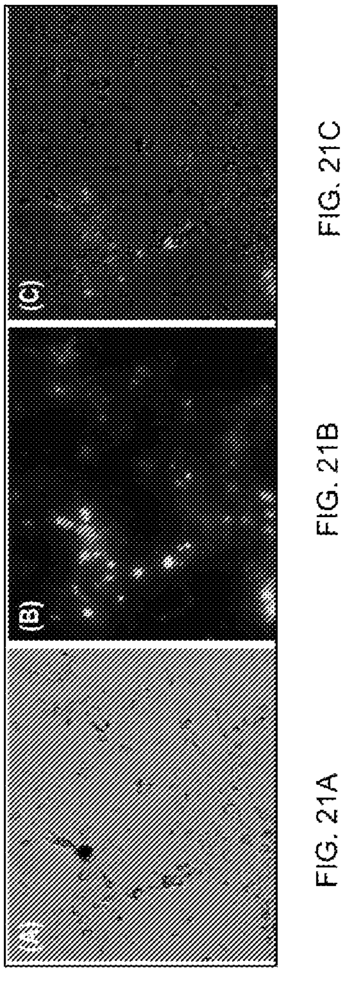
FIGS. 21A-21C provide human neural progenitor cells immunocytochemistry.

Isolated human neural progenitor cells were cultured in non-tissue culture treated dishes in media that promotes neural progenitor cells proliferation. As floating clusters began to form, cells were stained for neural crest-derived marker $p75^{NTR}$ by immunohistochemistry. FIG. 21 depicts a bright field forming cluster visualized of neural progenitor cells immunocytochemistry. FIG. 21 at panel (A) depicts that of isolated neural progenitor cells. FIG. 21 at panel (B) depicts that of neural progenitor cells stained positive for $p75^{NTR}$, neural crest-derived marker. FIG. 21 at panel (C) depicts the merged image. As can be seen, close to 100% of the neural progenitor cells stained positive for $p75^{NTR}$ indicating a successful isolation of the neural progenitor cells and further providing an indication of the purity of the culture.

Figure 22:
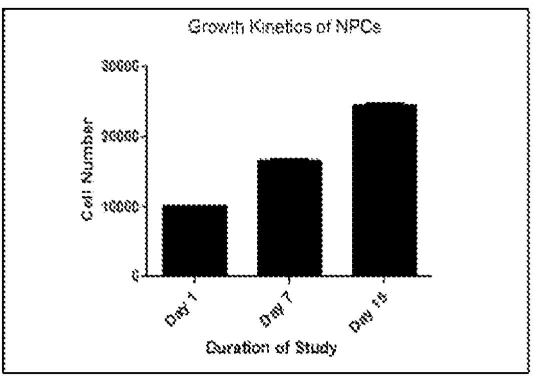
FIG. 22 is a graph showing growth kinetics of human neural progenitor cells.

Growth Kinetics:

FIG. 22 shows exemplary cell counting data. The human neural progenitor cells were counted and seeded into 6 well plates at a density of 10,000 neural progenitor cells per well for growth kinetics. Cell growth was followed over 15 days. The rate of proliferation of the neural progenitor cells was approximately 120% over a 15 day period. Cell number increased by approximately 55% between day 1 to day 7 and day 7 to day 15.

EXAMPLE 10

The present example discloses expanding, counting, and harvesting cells.

Expanding and Harvesting

Neural progenitor cells will be monitored for formation of cell clusters under microscope. When the cluster density reaches approximately 70%, cells are collected by centrifugation for 10 minutes at 2000×g and 15° C. The pellet is resuspended in 3-5 mL Accutase for 10 minutes, then neutralized using DMEM-F12 media. Cells are counted then centrifuged for 10 minutes at 200 g and 15° C. then resuspended in fresh neural growth media and re-plated and expanded to the desired number (~5 million).

When smooth muscle cells reach approximately 90% confluence, cells are harvested using TrypLE to release the cells from the plate and sub-cultured to expand to the desired number (~10 million). Cells are counted and the percent live cells recorded.

Six bioengineered Sphincter constructs are engineered per patient, necessitating a minimum of 3 million neural progenitor cells and 7.5 million smooth muscle cells. When the expanded cell numbers exceed these values, the cells are harvested for manufacturing the final product. During harvest, the spent media is collected to test for sterility, endotoxins, and gram-positive organisms. A sample of the cells in growth medium is also collected for measurement of cell count and viability, immunophenotyping or immunocytochemistry, and detection of mycoplasma, endotoxin, and gram-positive organisms before seeding.

EXAMPLE 11

The present example discloses forming a bioengineered human internal anal sphincter construct in accordance with the present disclosure.

Figures 23A, 23B, 23C, 23D:
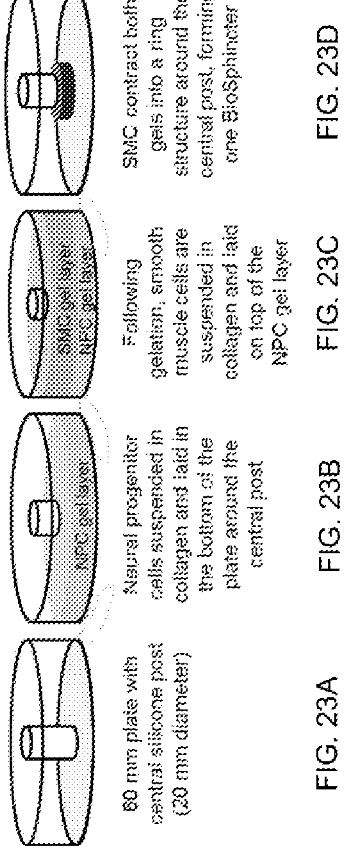
FIGS. 23A-23D depicts a schematic representation of a process of bioengineering an internal anal sphincter construct using autologous neural progenitor cells and smooth muscle cells in accordance with some embodiments of the present disclosure.

The design of the engineering process is summarized in FIG. 23. Generally, bioengineered internal anal sphincter constructs are generated using autologous neural progenitor cells and smooth muscle cells. FIG. 23 at panel (A) depicts a silicone mold and/or plate that is provided. The mold and/or plate is about 60 mm in diameter. The mold and/or plate has a central post. The mold and/or plate has a 20 mm in diameter. FIG. 23 at panel (B) depicts the neural progenitor cells that are isolated from the patient will be collected, suspended in collagen/laminin gel. The gel is then uniformly laid onto the prepared mold around the central post to gel for at least 20 minutes at 37° C. and 7% $CO_2$. FIG. 23 at panel (C) depicts the smooth muscle cells that are isolated from the patient are suspended in a collagen gel. The smooth muscle cell gel is layered on top of the gel containing the neural progenitor cells. This mixture will be allowed to gel for at least 45 additional minutes at 37° C. and 5% $CO_2$. FIG. 23 at panel (D) depicts, following gelation, adding differentiation media to the plate and/or mold. Subsequently, the smooth muscle cells contract both gels into a ring-like structure around the post to form one bioengineered internal anal sphincter construct. The bioengineered internal anal sphincter constructs are cultured for 12 days with media changes every other day.

Co-Culturing of Cells

Three million neural progenitor cells will be collected from the expanded culture and suspended in 12 mL of gel mixture including medical grade collagen, recombinant laminin, DMEM and water. Below Table 6 provides the gel composition for the neural progenitor cell gel, that is Table 6 outlines the gel layer compositions. The neural progenitor cells suspension will be gently mixed by pipetting and a 2-mL volume of the cell mixture dispensed by pipette around the central post in each of the 60 mm dishes. The dishes will then be gently swirled to ensure complete coverage of the dish and the mixture allowed to gel in the incubator at 37° C. with 7% $CO_2$ for at least 20 minutes or until gelation is observed.

During this time, smooth muscle cells will be prepared for plating. A total of 7.5 million smooth muscle cells will be collected from the expanded culture and suspended in 12 mL of gel mixture including medical grade collagen, DMEM and water. Below Table 6 provides the gel composition for the smooth muscle cell gel, that is Table 6 outlines the gel layer compositions. Dishes containing the neural progenitor cell gels will be transferred from the incubator to the BSC. The smooth muscle cell suspension will be gently mixed by pipetting and a 2-mL volume of the mixture dispensed by pipette on top of the first gel layer in each of the six dishes. The dishes will be returned to the incubator for 45 minutes to achieve complete gelation. Following gelation, neural differentiation media will be added to the dishes; subsequently, the media will be changed every other day until day 12.

TABLE 6

Composition of Each Gel Layer.

| | Gel Composition per 1 bioengineered Sphincter | |
|---|---|---|
| | Neural Progenitor Cells | Smooth Muscle Cells |
| Water | 915 μl | 945 μl |
| 4X DMEM | 500 μl | 500 μl |
| Collagen type 1 (4 mg/ml) | 500 μl | 500 μl |
| Titration Buffer | 55 μl | 55 μl |
| Laminin (1.2 mg/ml) | 30 μl | — |

Ultimately, the cell mixtures will coalesce and form a ring structure around the central post within 48 hours. The bioengineered internal anal sphincter complexes will mature by day 10-12.

EXAMPLE 12

The present example characterizes bioengineered human internal anal sphincter constructs formed in accordance with methods disclosed herein.

In some embodiments, a bioengineered internal anal sphincter has a ring structure with a central lumen. In these example embodiments, an internal diameter of the bioengineered internal anal sphincter can average about 20 mm. In these example embodiments, a surface area of the bioengineered internal anal sphincter can average about 169.8±0.6 $mm^2$ and volume average 181.7±0.3 $mm^3$. In these example embodiments, a thickness of the bioengineered internal anal sphincter can average about 2.3±0.01 mm. In these example embodiments, a height of the bioengineered internal anal sphincter can average about 2.4±0.009 mm.

Figures 24A, 24B:
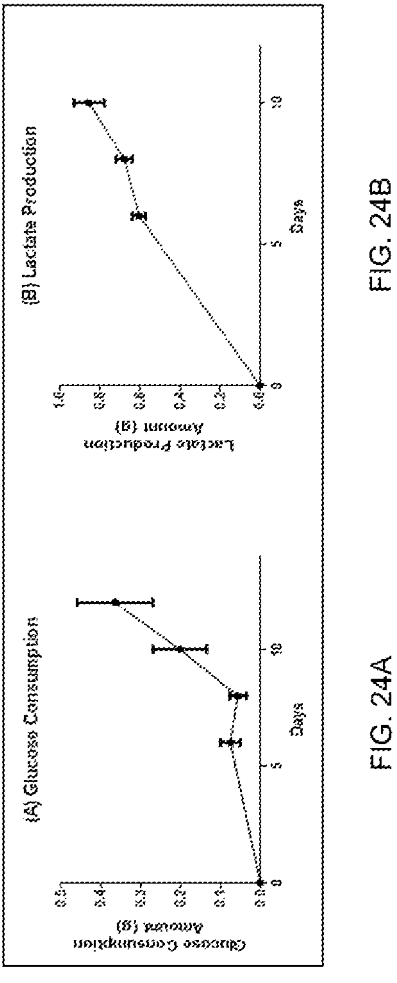
FIGS. 24A-24B provide exemplary data showing glucose consumption and lactate production.

Glucose/Lactate Assay:

Spent media was collected at the time of media changes during the culture process for the bioengineered internal anal sphincter constructs. FIG. 24 depicts exemplary data showing glucose consumption and lactate production in the bioengineered internal anal sphincter constructs. Media was collected at media changes starting at day 6 following bioengineering and until harvest at day 12. The amount of glucose and lactate was measured in the collected media in order to assess cellular metabolism. FIG. 24 at panel (A) depicts exemplary data of the analysis of media for glucose consumption. FIG. 24 at panel (B) depicts exemplary data of the analysis of media for lactate production. The exemplary data of these assays showed that both levels glucose consumption and levels lactate production were significantly increased in the bioengineered internal anal sphincter constructs over the days of the study (n=4; mean±SEM).

Figures 25A, 25B, 25C, 25D:
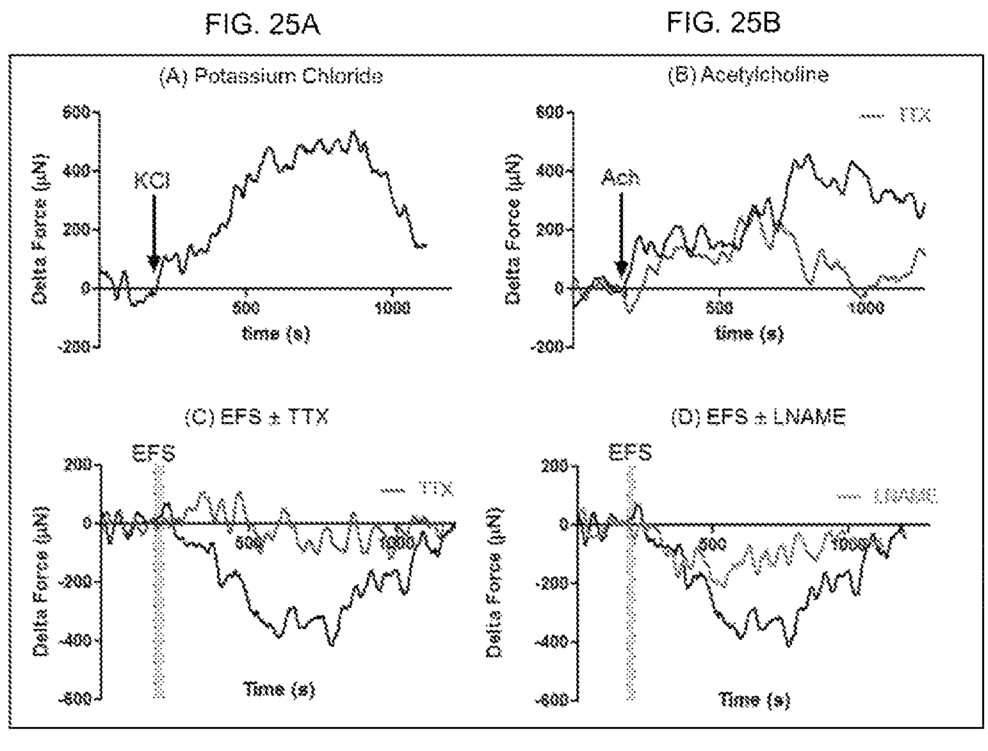
FIGS. 25A-25D provide exemplary basal tone data showing physiological functionality of bioengineered human internal anal sphincter constructs, in particular assessing functionality of the components, smooth muscle cells and neural progenitor cells.

Physiological Functionality:

Bioengineered internal anal sphincter constructs were analyzed for the functionality of both smooth muscle cells and neural progenitor cell components at day 12 post-bioengineering by measuring real-time force generation on an isometric force transducer. FIG. 25 depicts exemplary data showing physiological functionality of bioengineered internal anal sphincter constructs.

Briefly, bioengineered internal anal sphincter constructs were incubated in fresh 37° C. HEPES buffer to establish a baseline for basal tone and then treated with 60-mM KCl to induce depolarization of the smooth muscle membrane. FIG. 25 at panel (A) shows KCl-induced depolarization results in smooth muscle contraction (average 461±8 μN). Smooth muscle contraction in response to membrane depolarization reflects maintenance of functional voltage-dependent Ca2+ channels in the smooth muscle cells within the bioengineered internal anal sphincter constructs.

Bioengineered internal anal sphincter constructs were also tested for contractility in response to the major excitatory neurotransmitter in the gut, Acetylcholine. As shown in FIG. 25 at panel (B), treatment with exogenous Acetylcholine (10 μM) results in contraction of the bioengineered internal anal sphincter constructs with an average peak contraction of 352±6 μN. To distinguish between the muscle and neural contribution of the response, bioengineered internal anal sphincter constructs were washed, incubated in fresh buffer and treated with tetrodotoxin (TTX), an inhibitor of voltage-gated Na+ nerve channels. As shown in FIG. 25 at panel (B) (red trace), treatment with Acetylcholine (10 μM) under this condition induced a lower level of contraction that averaged 171±13 μN.

These results demonstrate that both smooth muscle and neural components of the bioengineered internal anal sphincter constructs responded to Acetylcholine.

The bioengineered internal anal sphincter constructs were also tested by using electrical field stimulation (EFS). Electrical field stimulation (parameters: 5 Hz, 0.5 ms) was applied to the construct with parallel platinum plate electrodes in the organ bath and resulted in a relaxation response with maximal relaxation averaging −370±6 μN, as shown in FIG. 25 at panel (C). Relaxation was abolished by TTX pretreatment, FIG. 25 at panel (C) (red trace).

To further characterize the relaxation, bioengineered internal anal sphincter constructs were also pre-treated with nitric oxide synthase inhibitor, N(ω)-nitro-L-arginine methyl ester (L-NAME; 300 μM, nNOS inhibitor) followed by EFS. Relaxation was partially inhibited (~50% inhibition), indicating the presence of functional nitric oxide neural population that contributed to the relaxation response, FIG. 25 at panel (D) (green trace). Together, these results demonstrate that the neural progenitor cells populating in the constructs differentiate into functional neurons by day 12 post-bioengineering.

Viability:

Bioengineered internal anal sphincter constructs were harvested on day 1, day 6, and day 12 for an MTT (3-[4, 5-dimethylthiazol-2-yl]-2, 5 diphenyl tetrazolium bromide) dye reduction assay. The viability of both neural progenitor cells and smooth muscle cells in bioengineered internal anal sphincter constructs was followed from day 1 up to day 12 post-bioengineering.

The MTT assay was carried out with cell-seeded scaffolds at different time intervals. The absorbance was considered directly proportional to the number of live, metabolically active and growing cells. Cells at day 0 of engineering were also harvested and used for standard curve generation. Bioengineered internal anal sphincter constructs were homogenized and incubated with 0.5 mg/mL MTT solution for 4 hours at 37° C. During this incubation, the MTT reagent is reduced by the cells to purple formazan crystals that can be detected spectrophotometrically at 570 nm.

Figure 26:
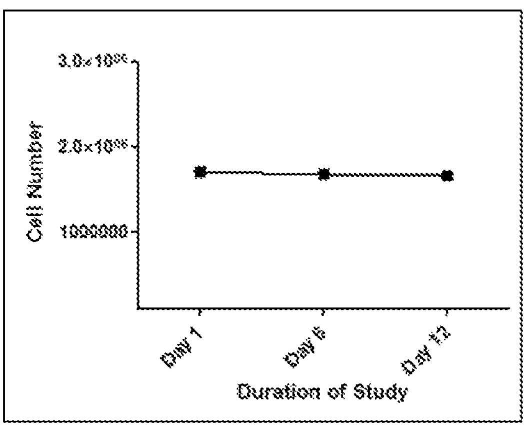
FIG. 26 is a graph with exemplary data using MTT assay for a curve used to extrapolate the number of cells in the bioengineered human internal anal sphincter constructs at various time points.

FIG. 26 depicts exemplary data for a standard curve for cell number generated and used to extrapolate the number of cells in the bioengineered internal anal sphincter constructs at various time points. Viability of the bioengineered internal anal sphincter constructs was followed from day 1 up to day 12 post-bioengineering using MTT assay. Cell viability did not significantly change from day 1 to day 12, indicating maintenance of the integrity of the cells. The total number of viable cells dropped slightly by 3% from day 1 to day 12 as an indication of viability of bioengineered internal anal sphincter constructs, which was not statistically significant.

Figures 27A, 27B:
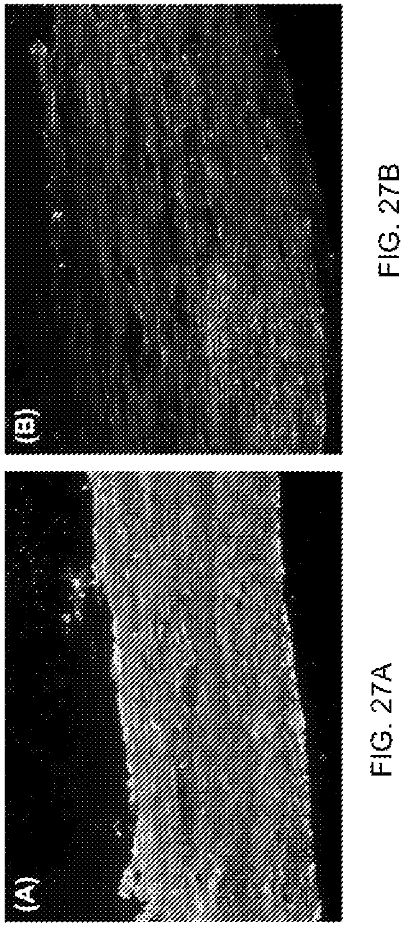
FIGS. 27A-27B depicts immunohistochemistry of bioengineered human internal anal sphincter constructs.

Histology:

Bioengineered internal anal sphincter constructs were fixed and processed for histological analysis after day 12 post-bioengineering. Immunofluorescence studies were performed. Slides were de-paraffinized and hydrated to water. Slides were blocked using serum followed by permeabilization. Immuno-histochemical analysis was performed with antibody specific for α-smooth muscle actin, conjugated with green fluorescent protein. FIG. 27 depicts exemplary immunochemistry of bioengineered internal anal sphincter constructs. FIG. 27 at panel (A) depicts exemplary fluorescence microscopy used to visualize positive staining for smooth muscle actin, and indicated maintenance of the smooth muscle phenotype in the construct. Additionally, cells of the constructs were tested for the neural marker βIII-tubulin. FIG. 27 at panel (B) depicts exemplary fluorescence microscopy of positive βIII-tubulin observed, indicating that the neural progenitor cells in the bioengineered internal anal sphincter constructs had differentiated into mature neurons.

Stability of Bioengineered Internal Anal Sphincter Constructs

Stability of bioengineered internal anal sphincter constructs was studied for up to 48 hours. The sphincters were bioengineered as described above and cultured for 12 days. On day 12 (day for clinical implantation), 6 bioengineered internal anal sphincter constructs were incubated in transport media (Neurobasal-A media) at different temperatures: 15° C. (n=2), 20° C. (n=2) and 25° C. (n=2) for 48 hours. Bioengineered internal anal sphincter constructs incubated at 37° C. were used as controls. Physiological functionality and viability assay were conducted to test the stability.

Figure 28:
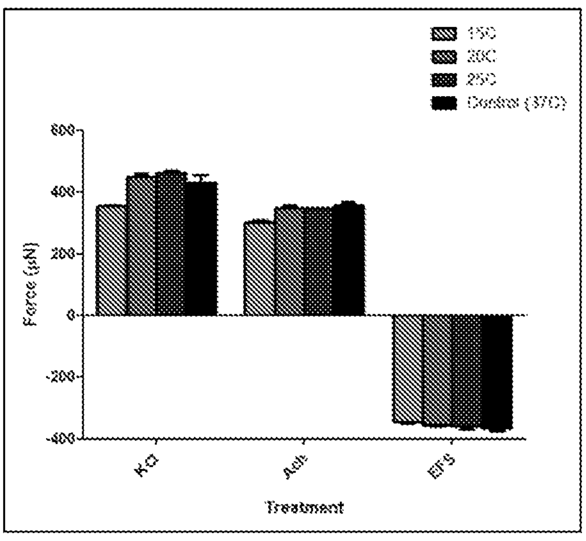
FIG. 28 is a graph with exemplary data showing physiological functionality of bioengineered internal anal sphincter constructs stored at different temperatures for up to 48 hours.

Physiological Functionality:

Bioengineered internal anal sphincter constructs incubated at different temperatures (15° C., 20° C., and 25° C.) for up to 48 hours were acclimated 1-2 hr at 37° C. and tested for physiological functionality as described above. Bioengineered internal anal sphincter constructs incubated at 37° C. for up to 48 hours were used as a control. All bioengineered internal anal sphincter constructs contracted in response to KCl to a similar extent without significant difference. Bioengineered internal anal sphincter constructs contracted similarly in response to exogenous Ach without significant difference. EFS resulted in relaxation of the bioengineered internal anal sphincter constructs to a similar extent. Together, these results demonstrate that bioengineered internal anal sphincter constructs stored in Neurobasal-A media for up to 48 hours at 15° C., 20° C., or 25° C. maintain muscle and neural function that is comparable to control conditions. FIG. 28 depicts exemplary data showing physiological functionality of bioengineered internal anal sphincter constructs stored at different temperatures for up to 48 hours. Bioengineered internal anal sphincter constructs responded similarly to stimulation of both smooth muscle and neural components (n=2).

Below Table 7 provides a summary of the force values means. The summary of physiological functionality results of the bioengineered internal anal sphincter constructs stored at different temperatures for up to 48 hours compared to control. Data showed no significant difference in bioengineered internal anal sphincter constructs functionality when stored at temperatures lower than 37° C. for up to 48 hours, bioengineered internal anal sphincter constructs performed similarly (n=2 per condition).

TABLE 7

Physiological Functionality Testing of constructs at Different Temperatures

| | Force ± SEM (μN) | | |
|---|---|---|---|
| | KCl | ACh | EFS |
| Control 37° C. | 432 ± 26 | 360 ± 10 | −367 ± 9 |
| 25° C. | 465 ± 5 | 350 ± 10 | −360 ± 10 |
| 20° C. | 450 ± 10 | 350 ± 10 | −355 ± 5 |
| 15° C. | 355 ± 5 | 305 ± 5 | −345 ± 5 |

Figure 29:
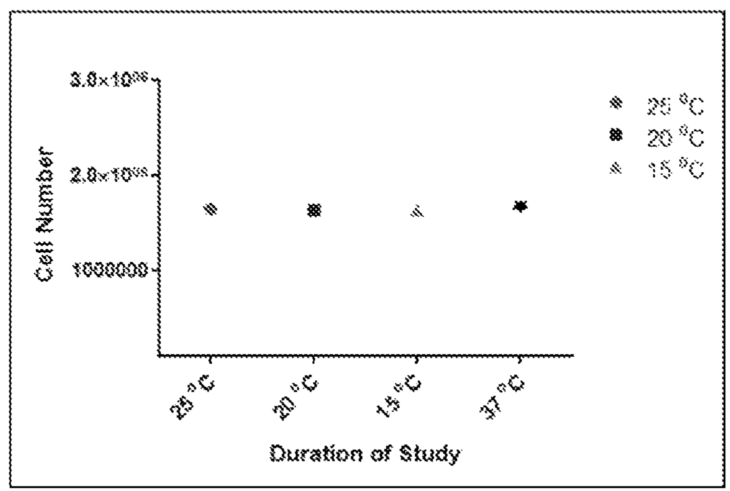
FIG. 29 is a graph with exemplary data showing viability of bioengineered internal anal sphincter constructs at different temperatures for up to 48 hours.

Viability Assay:

Bioengineered internal anal sphincter constructs stored at 15° C., 20° C., or 25° C. for up to 48 hours were also tested for changes in cell viability. FIG. 29 depicts exemplary data showing viability of bioengineered internal anal sphincter constructs at different temperatures. No significant changes in cell viability were observed in bioengineered internal anal sphincter constructs stored under these conditions when compared to control (37° C.) for up to 48 hours. These results were consistent with the results obtained for physiological functionality assessment under the same conditions.

Taken together, these results indicate that bioengineered internal anal sphincter constructs are stable for up to 48 hours at temperatures ranging from 15° C. to 37° C.; and establishes 48 hours as the point of expiry for the bioengineered internal anal sphincter constructs.

The present disclosure is not limited to the embodiments described and exemplified above but is capable of variation and modification within the scope of the appended claims. The section headings used herein are for organizational purposes only and are not to be construed as limiting. While the applicant's teachings are described in conjunction with various embodiments, it is not intended that the applicant's teachings be limited to such embodiments. On the contrary, the applicant's teachings encompass various alternatives, modifications, and equivalents, as will be appreciated by those of skill in the art.

Various publications, including patents, published applications, technical articles and scholarly articles are cited throughout the specification. Each of these cited publications is incorporated by reference herein, in its entirety and for all purposes.

While the present disclosure has explicitly discussed certain particular embodiments and examples of the present disclosure, those skilled in the art will appreciate that the disclosure is not intended to be limited to such embodiments or examples. On the contrary, the present disclosure encompasses various alternatives, modifications, and equivalents of such particular embodiments and/or example, as will be appreciated by those of skill in the art.

Accordingly, for example, methods and diagrams of should not be read as limited to a particular described order or arrangement of steps or elements unless explicitly stated or clearly required from context (e.g., otherwise inoperable). Furthermore, different features of particular elements that may be exemplified in different embodiments may be combined with one another in some embodiments.

What is claimed is:

1. A method of generating an innervated internal anal sphincter construct, comprising the following steps:

the step of obtaining an anorectum tissue cell biopsy from a subject;

the step of obtaining an intestinal tissue cell biopsy from the subject;

the step of isolating smooth muscle cells from the anorectum tissue cell biopsy;

the step of culturing the isolated smooth muscle cells for about four weeks until the number of smooth muscle cells reaches at least about 10 million cells;

the step of isolating neural progenitor cells from the intestinal tissue cell biopsy;

the step of culturing the isolated neural progenitor cells for about four weeks until the number of neural progenitor cells reaches at least about five million cells;

the step of preparing a smooth muscle cell gel by suspending the isolated smooth muscle cells in a gel matrix, to provide a first gel layer which is a smooth muscle gel layer;

the step of preparing a neural progenitor cell gel by suspending the isolated neural progenitor cells in a gel matrix to provide a second gel layer which is a neural progenitor cell gel layer;

the step of depositing the first smooth muscle gel layer around a central post of a culture plate or in a mold which is in a substantially circular shape, followed by depositing the second neural progenitor cell gel layer on top of the first smooth muscle cell layer around a central post of a culture plate or in a mold which is in a substantially circular shape to form a dual layer gel matrix, wherein the first smooth muscle gel layer and the second neural progenitor cell gel layer of the dual layer gel matrix are in contact;

the step of contacting the dual-layer gel matrix with a differentiation media to induce differentiation of the neural progenitor cells into functional neurons, thereby forming the innervated internal anal sphincter construct having directionally oriented smooth muscle cells, further wherein the innervated internal anal sphincter construct is capable of treating fecal incontinence when implanted in a subject.

2. The method of claim 1, wherein the step of obtaining the anorectum tissue cell biopsy further comprises a step of obtaining the biopsy from the subject's internal anal sphincter tissue.

3. The method of claim 1, wherein the step of obtaining the intestinal tissue cell biopsy further comprises obtaining the biopsy from the subject's jejunal small intestine tissue.

4. The method of claim 1, wherein at least one of the steps of obtaining the anorectum tissue cell biopsy and obtaining the intestinal tissue cell biopsy is performed laparoscopically.

5. The method of claim 1, wherein the step of isolating smooth muscle cells from the anorectum tissue cell biopsy comprises the step of mechanically disaggregating the anorectum tissue cell biopsy.

6. The method of claim 1, wherein the step of isolating smooth muscle cells from the anorectum tissue cell biopsy comprises enzymatically digesting the biopsied anorectal tissue by applying a digesting medium.

7. The method of claim 6, wherein the digesting medium comprises a collagenase and optionally further comprises applying another protease, or combination thereof.

8. The method of claim 1, wherein the step of isolating smooth muscle cells from the anorectum tissue cell biopsy further comprises the steps of mechanically disaggregating the anorectum tissue cell biopsy, and subjecting the cells to enzymatic treatment with collagenase and/or protease, and the step of suspending disaggregated digested smooth muscle cells in a smooth muscle cell growth medium.

9. The method of claim 8, wherein the smooth muscle cell growth medium comprises a Smooth Muscle Basal Medium optionally supplemented with fetal bovine serum, L-glutamine and/or an antibiotic/antimycotic agent.

10. The method of claim 1, wherein the step of isolating neural progenitor cells from the intestinal tissue cell biopsy comprises the step of mechanically disaggregating the intestinal tissue cell biopsy.

11. The method of claim 1, wherein the step of isolating neural progenitor cells from the intestinal tissue cell biopsy comprises enzymatically digesting the intestinal tissue cell biopsy with a digesting medium.

12. The method of claim 11, wherein the digesting medium comprises a collagenase, or another protease, or combinations thereof.

13. The method of claim 1 wherein the step of isolating neural progenitor cells from the intestinal tissue cell biopsy comprises the step of suspending the isolated neural progenitor cells in a neural growth medium.

14. The method of claim 13, wherein the neural growth medium comprises a neural basal medium, one or more growth factors, L-Glutamine, and/or an antibiotic/antimycotic agent.

15. The method of claim 1, wherein prior to seeding the multi-layer gel matrix, the method further comprises the step of preparing at least one gel layer of isolated smooth muscle cells by suspending the isolated smooth muscle cells in a gel matrix material comprising collagen.

16. The method of claim 1, wherein prior to seeding the multi-layer gel matrix, the method further comprises the step of preparing at least one gel layer of isolated neural progenitor cells by suspending the isolated neuronal progenitor cells in a gel matrix material comprising collagen and laminin.

17. The method of claim 1, further wherein the mold comprises a central post and the step of seeding comprises depositing the gel layers around the central post.

18. The method of claim 1, further comprising the step of removing the construct from the culture plate or mold.

* * * * *